(12) United States Patent
Roberts et al.

(10) Patent No.: US 8,367,735 B2
(45) Date of Patent: Feb. 5, 2013

(54) PHARMACEUTICAL COMPOSITIONS

(75) Inventors: Stanley M. Roberts, Manchester (GB); Gabriella M. Santoro, Rome (IT)

(73) Assignee: Crawford Healthcare Holdings Limited, Knutsford Cheshire (GB)

( * ) Notice: Subject to any disclaimer, the term of this patent is extended or adjusted under 35 U.S.C. 154(b) by 737 days.

(21) Appl. No.: 12/375,208

(22) PCT Filed: Jul. 26, 2007

(86) PCT No.: PCT/GB2007/050449
§ 371 (c)(1),
(2), (4) Date: Sep. 1, 2009

(87) PCT Pub. No.: WO2008/012583
PCT Pub. Date: Jan. 31, 2008

(65) Prior Publication Data
US 2009/0325901 A1    Dec. 31, 2009

(30) Foreign Application Priority Data
Jul. 26, 2006    (GB) .................................. 0614848.0

(51) Int. Cl.
*A61K 31/015*    (2006.01)
*A61K 31/12*    (2006.01)
*C07C 49/603*    (2006.01)

(52) U.S. Cl. ........ 514/675; 514/678; 514/690; 514/724; 514/764; 514/765; 568/303; 568/308; 568/376

(58) Field of Classification Search .................... 514/63, 514/675, 678, 690, 724, 764, 765; 435/29, 435/5; 556/418; 568/303, 308, 376
See application file for complete search history.

(56) References Cited

FOREIGN PATENT DOCUMENTS
JP    61-215366    9/1986
WO    WO-03/051807    6/2003

OTHER PUBLICATIONS

Marber et al., "Myocardial Protection after Whole Body Heat Stress in the Rabbit Is Dependent on Metabolic Substrate and Is Related to the Amount of the Inducible 70-kD Heat Stress Protein," Clin. Invest. 93, 1087-1094, (1994).
Feinstein e al., Heat Shock Protein 70 Suppresses Astroglial-inducible Nitric-oxide Synthase Expression by Decreasing NFkB Activation,: J. Biol. Chem. 271, 17724-17732, (1996).
Amici et al., Selective Inhibition of Virus Protein Synthesis by Prostaglandin A1: a Translational Block Associated with HSP70 Synthesis,: J. Virology 68, 6890-6897, (1994).
Santoro, M, "Stress -inducible Cellular Responses,". (Fiege U et al. eds, Birkhaóser Verlag, Basel Boston Berlin) pp. 337-357, (1996).
Santoro et al., "Prostaglandins with antiproliferative activity induce the synthesis of a heat shock protein in human cells," Proc. Nati. Acad. Sci. USA 86, 8407-8411, (1989).
Amici et al., "Antiproliferative prostaglandins activate heat shock transcription factor," Proc. Nati. Acad. Sci. USA 89, 6227-6231, (1992).
Santoro et al., "Prostaglandin a compounds as antiviral agents," Science 209, 1032-1034, (1980).
Santoro, M, "Antiviral activity of cyclopentenone prostanoids," Trends in Microbiology. 5, 276-281, (1997).
Rossi et al., "Inhibition of nuclear factor kB by prostaglandin A1: An effect associated with heat shock transcription factor activation," Proc. Natl. Acad. Sci. USA 94, 746-750, (1997).
Thanos et al. "NF-KB: A Lesson in Family Values," Cell 80, 529-532, (1995).
Rossi et al., "2-Cyclopenten-1-one, a New Inducer of Heat Shock Protein 70 with Antiviral Activity," J. Biological Chemistry. 271, 32192-32196, (1996).
Kondo et al., "Cyclopentenone Prostaglandins as Potential Inducers of Intracellular Oxidative Stress," J. Biological Chemistry, 296, 12076-12083, (2001).
Silverman, R. B., "The Organic Chemistry of Drug Design and Drug Action,":Academic Press; Inc., 336-338, (1992).
Flanagan et al., "What's your antidote?", Chemistry in Britain, 29-31, (2002),.
Meister et al.,"Glutathione," Am. Rev. Biochem., 52, 711-760, (1983).
Dauvergne et al., "Titanium mediated alkylidenation of substituted cycloalkenones: scope and limitations", 60(11), pp. 2551-2557, 2004.
International Search Report and Written Opinion for PCT/GB2007/050449, Jan. 14, 2008.

*Primary Examiner* — Sreeni Padmanabhan
*Assistant Examiner* — Sahar Javanmard
(74) *Attorney, Agent, or Firm* — Mintz Levin Cohn Ferris Glovsky and Popeo, P.C.

(57) ABSTRACT

The present invention relates to compounds of formula I or II:—wherein R is an alkyl, alkenyl, alkynyl, aryl, aralkyl, aralkenyl, or aralkynyl group, that may be substituted or unsubstituted, and that optionally includes at least one heteroatom in its carbon skeleton; $R^1$ is hydrogen, or an alkyl, substituted alkyl, alkenyl, alkynyl, aryl, substituted aryl, or aralkyl group; and $R^2$ is an alkyl, alkenyl, alkynyl, aryl, aralkyl, aralkenyl, or aralkynyl group containing 4-12 carbon atoms, that may be substituted or unsubstituted, and that optionally includes at least one heteroatom in its carbon skeleton; provided that in a compound of formula I, when $R^1$ is an iso-propyl or phenyl group, $R^2$ is not an acetyl or tert-butyldimethylsilyl group; and their use in therapeutic, diagnostic and research methods.

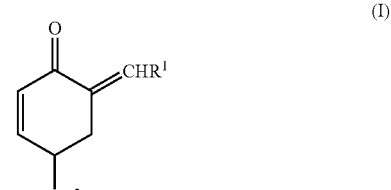

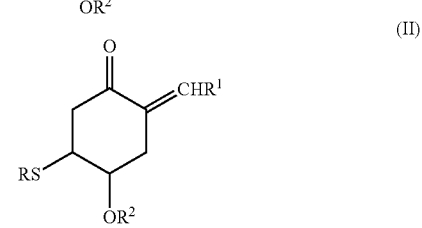

10 Claims, 7 Drawing Sheets

PHARMACEUTICAL COMPOSITIONS

The present invention relates to certain cyclohexenone and cyclohexanone derivatives. It also relates to the preparation of such derivatives, and to their use in medicine and other fields. The invention further relates to certain cyclohexanone derivatives with enhanced water solubility, lipophilicity and/or therapeutic indices, and to methods of enhancing the water solubility, lipophilicity and/or therapeutic indices of pharmaceutically active cyclohexenone derivatives.

Various compounds comprising the cyclopentenone ring structure (also known as the cyclopentenone nucleus) are capable of inducing the heat shock response. The heat shock response is a finely regulated and highly conserved mechanism to protect cells against different types of injury, including extreme temperatures, oxidative stress, exposure to toxins and viral infection (1). In human cells, triggering of the heat shock response requires activation of a transregulatory protein, the heat shock transcription factor type 1 (HSF1), which controls the expression of cytoprotective heat shock proteins (HSPs) (1). Whereas HSP induction was at first interpreted as a signal for detection of physiological stress, it is now accepted that HSPs are utilised by cells as molecular chaperones in the repair process following different types of injury to prevent damage resulting from the accumulation and aggregation of non-native proteins (1). In particular, a cytoprotective role of the heat shock protein HSP70 has now been described in a wide variety of human diseases, including ischemia, inflammation and viral infection (2-5). For these reasons HSF1 is considered a novel, attractive target for cytoprotective and antiviral drugs. In the case of viral infection, Santoro et al. have shown that a class of prostaglandins (PGs) with potent antiviral activity function as HSP70 inducers via HSF1 activation (6,7).

The ability of prostaglandins of the A type (PGAs) to inhibit viral replication and prevent the establishment of persistent infections was first reported in 1980 (8). It is now well established that PGs containing an α,β-unsaturated carbonyl group in the cyclopentane ring structure (cyclopentenone PG, cyPG) possess activity against a wide variety of DNA and RNA viruses, including herpes viruses, paramyxo viruses, orthomyxo viruses and retroviruses in in vitro and in vivo experimental models (9). The mechanism of the antiviral activity is distinct from any other known antiviral agent and is thought to involve the induction of heat shock proteins and the inhibition of the transcription factor NF-κB (nuclear factor-κB) in the infected cell.

NF-κB is an inducible eukaryotic transcription factor which has a critical role in promoting inflammation and viral replication (11). In most cells, NF-κB exists in an inactive cytoplasmic complex, whose predominant form is a heterodimer composed of p50 and p65 subunits, bound to inhibitory proteins of the IκB family, usually IκBα, and is activated in response to primary (viruses, bacteria, UV) or secondary (inflammatory cytokines) pathogenic stimuli (12). Stimulation triggers rapid phosphorylation and degradation of IκBα, resulting in NF-κB translocation to the nucleus, where the factor binds to DNA at specific κB-sites, inducing a variety of genes encoding signalling proteins. Target genes include those coding for inflammatory and chemotactic cytokines, cytokine receptors and viral proteins. NF-κB is involved in many pathological events including progression of AIDS by enhancing HIV-1 transcription and is considered an attractive therapeutic target for novel antiviral and anti-inflammatory drugs (12). Santoro et al. have shown that cyclopentenone prostaglandins inhibit NF-κB activation and NF-κB dependent HIV-1 transcription in human cells, by preventing IκBα phosphorylation and degradation, and that this effect is strictly associated with HSF1 activation (11).

Santoro et al. have identified the molecular structure of natural prostaglandins responsible for HSF activation and NF-κB inhibition (13). One component of the PGA molecule, cyclopent-2-en-1-one (also known as 2-cyclopenten-1-one), at a concentration of 125-500 μM, has been shown to be able to activate HSF1 and to rapidly and selectively trigger the synthesis of cytoprotective HSP70. At the same concentration, cyclopent-2-en-1-one has been shown to be able to block NF-κB activation by chemical or physiological inducers. These effects are associated with antiviral activity during infection with rhabdoviruses (13).

A family of pharmaceutically active cyclohexenone and cyclohexanone derivatives is described in international patent application no. PCT/GB02/05708, published as WO03/051807. The experimental results set out in this document show members of this family of compounds to be potent activators of HSF and inhibitors of NF-κB activity. They also show such compounds to be potent inhibitors of HSV-1 and Sendai virus replication.

There is no suggestion in the literature, however, that any cyclohexenone or cyclohexanone derivatives with an exocyclic double bond α to the carbonyl carbon, have a capacity to exhibit biological activity of the above discussed nature.

Surprisingly, it has now been found that certain cyclohexenone and cyclohexanone derivatives with an exocyclic double bond α to the carbonyl carbon, are pharmaceutically active in at least one of the aforementioned ways.

According to a first aspect of the present invention, there is provided a compound of formula I or II

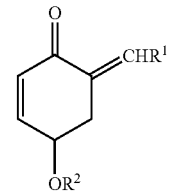

(I)

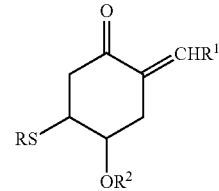

(II)

wherein:

R is an alkyl, alkenyl, alkynyl, aryl, aralkyl, aralkenyl, or aralkynyl group, that may be substituted or unsubstituted, and that optionally includes at least one heteroatom in its carbon skeleton;

$R^1$ is hydrogen, or an alkyl, substituted alkyl, alkenyl, alkynyl, aryl, substituted aryl, or aralkyl group; and $R^2$ is an alkyl, alkenyl, alkynyl, aryl, aralkyl, aralkenyl, or aralkynyl group containing 4-12 carbon atoms, that may be substituted or unsubstituted, and that optionally includes at least one heteroatom in its carbon skeleton;

provided that in a compound of formula I, when $R^1$ is an iso-propyl or phenyl group, $R^2$ is not an acetyl or tert-butyldimethylsilyl group. R can be a substituted group. Preferred substituents are or include —OH, —$OR^4$, —SH, —$SR^4$, —$NH_2$, —$NHR^4$, —$N(R^4)_2$, —$N(R^4)_3^+$, —$CO_2H$, —$CO_2R^4$, —$NHCOR^4$, —$CONH_2$, —$CONHR^4$, and —$CON(R^4)_2$, wherein $R^4$ is an alkyl, aryl, or aralkyl group. Preferably, $R^4$ contains 1-12 carbon atoms.

R can be an $R^3CH_2$— group, such that the group —SR is an —$SCH_2R^3$ group, wherein $R^3$ is an alkyl, alkenyl, alkynyl, aryl, aralkyl, aralkenyl, or aralkynyl group, that may be substituted or unsubstituted, and that optionally includes at least one heteroatom in its carbon skeleton. R, preferably, contains 1-12 carbon atoms.

In preferred embodiments, R or $R^3$ includes at least one hydrophilic group. Said hydrophilic group can be or include a hydroxyl, carbonyl, carboxyl, amino, amido, quaternary ammonium or thiolyl group. R or $R^3$, therefore, can provide the functionality of an amine, amide, peptide, ester, carboxylic acid, carboxylic acid salt, alcohol, aldehyde, ketone or thiol to an inventive compound.

In further preferred embodiments, the group —SR is an S-cysteinyl or a substituted S-cysteinyl group. In the context of this application, a substituted or unsubstituted S-cysteinyl group comprises a cysteinyl moiety that is bound to the ring via its sulphur atom, with the ring replacing the hydrogen atom that is bound to the equivalent sulphur atom in cysteine. Preferred substituted S-cysteinyl groups include di- and tri-peptide groups that include an S-cysteinyl moiety, such as S-glutathionyl, S-cysteinyl ester and other like groups, including N-tert-butoxycarbonyl S-cysteinyl and N-tert-butoxycarbonyl S-cysteinyl ester (e.g. methyl and ethyl) groups.

$R^1$ is hydrogen, or an alkyl, substituted alkyl, alkenyl, alkynyl, aryl, substituted aryl, or aralkyl group. Preferably, $R^1$ contains 1-12 carbon atoms.

$R^1$ is preferably an aryl group and, more preferably, a phenyl group or substituted phenyl group.

$R^1$ can be a substituted group. Preferred substituents are or include a halo (fluoro, chloro, bromo, iodo), nitro, alkyl, and alkoxy group. If the substituents are or include an alkyl or alkoxy group, preferably, the alkyl or alkoxy group contains 1-6 carbon atoms.

$R^2$ is preferably an alkyl group that includes a heteroatom in its carbon skeleton. The heteroatom is preferably silicon and, in preferred embodiments, $R^2$ is a trialkylsilyl group, preferably a tert-butyldimethylsilyl group.

Alternatively, $R^2$ may be —$COR^5$, wherein $R^5$ is an alkyl, alkenyl, alkynyl, aryl, aralkyl, aralkenyl, or aralkynyl group containing 3-11 carbon atoms, that may be substituted or unsubstituted, and that optionally includes at least one heteroatom in its carbon skeleton. Preferably, $R^5$ is an alkyl group containing 3-6 carbon atoms, preferably a tert-butyl group.

$R^2$ can be a substituted group. Preferred substituents are or include an alkoxy group, preferably containing 1-6 carbon atoms.

Each of R, $R^2$ and $R^3$ can independently be a group that includes at least one heteroatom in its carbon skeleton. Preferred heteroatoms are oxygen, nitrogen, sulphur and silicon.

Compounds of formula (I) in accordance with the invention have at least one chiral centre (*) and can therefore exist in the form of a least two enantiomers. Compounds of formula (II) in accordance with the invention have at least two chiral centres (*) and can therefore exist in the form of a least four enantiomers. All such enantiomers, unequal mixtures thereof and racemates are encompassed by the present invention. Both R- and S-enantiomers of the compounds of formula (I) and all four RR-, SS-, RS- and SR-enantiomers of the compounds of formula (II) are useful. They can each be provided in a form substantially free of the other enantiomer(s) (e.g. at least 75%, 85%, 90%, 95% or 99% free (w/w)). Mixtures of enantiomers (e.g. unequal or racemic mixtures) may however also be used.

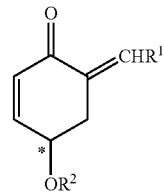

(I)

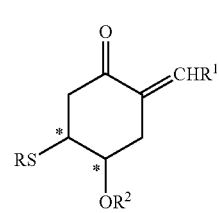

(II)

Compounds in accordance with the invention, for which $R^1$ is not hydrogen, exist in both Z and E forms, i.e. with $R^1$ being cis- or trans- to the carbonyl carbon in the cyclohexenone or cyclohexanone ring. The present invention encompasses all such individual isomers and mixtures thereof, together with their uses.

A preferred compound in accordance with the first aspect of the present invention includes the following:—

(CTM-208)

Other preferred compounds in accordance with the first aspect of the present invention include the following:—

(CTM-208-2R,1'S,2'S)

(CTM-208-2R,1'R,2'R)

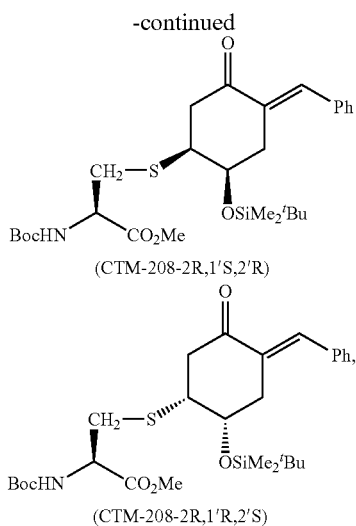

(CTM-208-2R,1'S,2'R)

(CTM-208-2R,1'R,2'S)

and mixtures of these enantiomers, for example, a 50:50 mixture of (CTM-208-2R,1'S,2'S) and (CTM-208-2R,1'R,2'R).

Compounds in accordance with the invention may be prepared by the techniques described in the examples. In particular, compounds of formula I may be prepared by a technique of the type described in general method A (see below), and compounds of formula II may be prepared from their cyclohexenone analogues of formula I by a technique of the type described in general method B (see below).

Many pharmaceutically active compounds are poorly soluble in water or highly lipophilic. Such compounds are less suited, therefore, to being administered to patients orally than by other routes of systemic administration, that are generally less favoured by patients, such as by parenteral injection. Moreover, such compounds are often biologically active in a manner that suggest usefulness in the topical treatment of skin conditions such as, for example, psoriasis and skin cancers. However, many are insufficiently lipophilic to penetrate the skin to the degree required to be therapeutically effective in such treatments.

The therapeutic index of a drug or pharmaceutically active compound is indicated by the ratio of its median lethal dose, or $LD_{50}$, to its medium effective dose, or $ED_{50}$. Because its use would generally involve a lower risk of causing toxic side effects in individual patients given a therapeutically effective dose, a compound with a larger therapeutic index would normally be preferred over an alternative with a smaller therapeutic index. Accordingly, if the therapeutic index of a particular pharmaceutically active compound could be increased without ill effect, this would be an attractive result.

Preferred compounds of formula II are:—
  (a) more soluble in water at a temperature of 20-40° C.;
  (b) less lipophilic; and/or
  (c) have a greater therapeutic index; or
  (d) less soluble in water at a temperature of 20-40° C.;
  (e) more lipophilic; and/or
  (f) have a greater therapeutic index;
than equivalent compounds of formula I. An equivalent compound of formula I to a preferred compound of formula II is a compound with, excepting the absent —SR group and an additional hydrogen atom in the 2 position in the six membered ring, the same substitution pattern as the preferred compound of formula II.

Where a preferred compound in accordance with the invention is required to be less lipophilic than an "equivalent" compound, this means that the ratio of n-octanol to aqueous solubility (i.e. the n-octanol/water partition coefficient) for the preferred compound is lower than it is for the "equivalent" compound. Similarly, where a preferred compound in accordance with the invention is required to be more lipophilic than an "equivalent" compound, this means that the ratio of n-octanol to aqueous solubility (i.e. the n-octanol/water partition coefficient) for the preferred compound is higher than it is for the "equivalent" compound. The ratio of n-octanol to aqueous solubility is usually expressed in terms of its base ten logarithm, "log P", and a compound with a log P value of 1 will be 10 times more soluble in n-octanol than it is in water, a compound with a log P value of 2 will be 100 times more soluble in n-octanol than it is in water and so on. Log P values can be measured by experiment, or calculated using one of several available computer programs or algorithms. Examples of these include the Pomona College Medicinal Chemistry program, the MacLogP application from BioByte Corp. (Claremont USA), and the method described by Moriguchi et al. (20). Thus, it is preferred that compounds, required in this specification to be less lipophilic (or have greater water solubility) than equivalent compounds, will have lower log P values than such equivalents, and that compounds, required in this specification to be more lipophilic (or be less water soluble) than equivalent compounds, will have higher log P values than such equivalents. In this context, the log P values are preferably calculated values derived from applying one of the aforementioned programs or algorithms.

For each compound of formula I, there are many compounds of formula II that differ from each other solely by the nature of their —SR substituents. The useful biological and pharmacological properties of equivalent compounds of formula I are often retained and sometimes even enhanced in the related —SR substituted compounds of formula II. It has also been found that the lipophilicity and water solubility of compounds of formula II is highly dependent upon the nature of the —SR group which they carry. In essence, increasing the lipophilicity of the group R (in the —SR substituent) will result in a compound of formula II that is more lipophilic and less water soluble, and vice versa, and the degree to which the lipophilicity or water solubility of an equivalent compound of formula I can be manipulated in this way is sufficient for many such compounds to be "adaptable" for both topical and oral use. Thus, compounds of formula II provide those skilled in the art with the means to adapt the physical properties of any given equivalent compound of formula I to suit a particular mode of delivery, e.g. oral or topical, without prejudicing its pharmacological properties. This represents a highly significant and surprising advantage of the present invention.

Where a preferred compound in accordance with the invention is required to have a greater therapeutic index than an "equivalent", this relationship must hold true for at least one therapeutic application. For the purposes of this specification, the existence of such a relationship can be established either by observation of in vivo effects, or via in vitro tests or assays of the type conventionally employed by persons skilled in the art for the purpose of predicting the therapeutic indices of putative drug substances. For example, an assay for one of the properties discussed below could be used in combination with a toxicity assay, to provide the required information for a particular pair of inventive compound and equivalent. Examples of appropriate assays are set out in Examples 2 and 3 below.

Certain preferred compounds of formula II have calculated or measured log P values that are at least 0.25, 0.5, 0.75, 1 or 1.25 higher or lower than the log P values for their equivalents of formula I, wherein the log P values for each compound of formula II and its equivalent of formula I are calculated or measured using the same technique. In embodiments, compounds of formula II have a log P value of 5 or less, and preferably of no more than 4.15, 4, 3, 2, or 1, when calculated by the method described by Moriguchi et al. (20). Compounds with log P values in these latter preferred ranges are generally more readily absorbed from the gastro-intestinal tract and, therefore, are more suited to oral administration, see Lipinski et al. (21). In alternative embodiments, compounds of formula II can have a log P value of at least 3.5, 4.2, or 5 and preferably of up to 6 or 7 and such compounds are suitable, therefore, for use in topical formulations for application to the skin.

As noted, R can be an $R^3CH_2$— group, such that the group —SR is an —$SCH_2R^3$ group, wherein $R^3$ is an alkyl, alkenyl, alkynyl, aryl, aralkyl, aralkenyl, or aralkynyl group, that may be substituted or unsubstituted, and that optionally includes at least one heteroatom in its carbon skeleton. R, preferably, contains 1-12 carbon atoms.

In those compounds of formula II which are more water soluble and/or less lipophilic than the equivalent compounds of formula I, the group R or $R^3$, preferably, includes at least one hydrophilic group. Said hydrophilic group can be or include a hydroxyl, carbonyl, carboxyl, amino, amido, quaternary ammonium or thiolyl group. In such compounds, therefore, R or $R^3$ can provide the functionality of an amine, amide, peptide, ester, carboxylic acid, carboxylic acid salt, alcohol, aldehyde, ketone or thiol to an inventive compound. In preferred such compounds the group —SR is an S-cysteinyl or a hydrophilic substituted S-cysteinyl group. Preferred substituted S-cysteinyl groups include di- and tri-peptide groups that include an S-cysteinyl moiety, such as an S-glutathionyl group.

In those compounds of formula II which are less water soluble and/or more lipophilic than the equivalent compounds of formula I, the group R or $R^3$, preferably, includes at least one lipophilic group and/or is lipophilic. Such lipophilic groups include substituted and unsubstituted alkyl, alkenyl, alkynyl, aryl, aralkyl, aralkenyl, or aralkynyl groups that, optionally, include at least one heteroatom in their carbon skeletons, but which do not carry any substituents that render them hydrophilic. Preferred such groups include substituted and unsubstituted phenyl and naphthyl groups and N-tert-butoxycarbonyl S-cysteinyl ester (e.g. methyl and ethyl) groups.

As has been noted, an advantage of certain compounds of formula II is that, because they are less lipophilic and/or more soluble in water at around room temperature and/or body temperature than are analogous compounds of formula I that do not include an —SR substituent, they are more suited to use in orally administered pharmaceutical compositions. Thus, in a further preferred aspect, the present invention provides pharmaceutical compositions for oral administration, comprising a compound of formula II that is more soluble in water at a temperature of 20-40° C. and/or less lipophilic than an equivalent compound of formula I in which a hydrogen atom replaces said —SR group. Such compositions can include one or more pharmaceutically acceptable diluent, carrier and/or other excipient suitable for use in compositions for oral administration.

As has also been noted, an advantage of certain other compounds of formula II is that, because they are more lipophilic and/or less soluble in water at around room temperature and/or body temperature than are analogous compounds of formula I that do not include an —SR substituent, they are more suited to use in pharmaceutical compositions for topical administration, particularly to the skin. Thus, in a yet further preferred aspect, the present invention provides pharmaceutical compositions for topical administration, preferably to the skin, comprising a compound of formula II that is less soluble in water at a temperature of 20-40° C. and/or more lipophilic than an equivalent compound of formula I in which a hydrogen atom replaces said —SR group. Such compositions can include one or more pharmaceutically acceptable diluent, carrier and/or other excipient suitable for use in compositions for topical administration.

Moreover, because the pharmaceutically active compounds of formula II can also have a greater therapeutic index than their equivalents without an —SR substituent, they are potentially more useful in a therapeutic context.

In the pharmaceutical industry, a major problem with any potential drug is that it may be very biologically active but somewhat toxic. For example, an anti-tumour drug must be toxic towards certain groups of cells but not potentially harmful to other cells.

Cyclopentenone compounds are known to undergo Michael reactions with glutathione in the cell. Glutathione is found throughout the body and plays crucial roles in protecting cells from oxidative damage (maintaining redox balance). In this regard, work by Uchida et al. (22) and others has suggested a role for glutathione in protecting cells from oxidative stress as a radical scavenger. Uchida's work showed that cells with depleted glutathione retain higher concentration of radical oxygen species. It also demonstrated that, when such cells were treated with N-acetyl-cysteine and cell viability was measured, an increase in cell life and a decrease in the production of radical oxygen species was observed. Uchida et al. came to the conclusion that species capable of reducing glutathione levels in the cell, also reduce the cell's anti-oxidant defences and increase the induction of radical oxygen species. They also showed that cyclopentenone mediated production of radical oxygen species was well correlated with cytotoxicity and, thus, demonstrated a potentially important mode of cytotoxicity or induction of cell death by cyclopentenone compounds.

Glutathione is also known to protect cells from dangerous electrophilic species. For example, morphine type compounds undergo a Michael reaction with glutathione that results in complete deactivation of the drug (23). If large amounts of paracetamol (acetaminophen) are taken then glutathione in the liver is depleted [in 1999 there were 150 deaths in the UK from paracetamol poisoning]. If N-acetyl cysteine is taken intravenously or orally less than 15 hours after the overdose, it effectively removes the offending electrophilic paracetamol metabolite (24).

Other studies have shown that a reduction of intracellular thiol content can increase the sensitivity of turnout cells to radiation treatment. Moreover, cells exhibiting depleted levels of glutathione have been shown to be more susceptible to radiation, chemotherapeutic agents and oxygen radical species that otherwise would have been destroyed via radical reaction with glutathione (25).

A glutathione group cannot be added to a saturated moiety, such as a cyclohexanone group, via a Michael reaction. Thus, unless they are metabolised into the equivalent unsaturated cyclohex-2-en-1-ones, compounds in accordance with the invention that comprise a cyclohexanone group may be less likely to react with glutathione in vivo than are these unsaturated equivalents. Such saturated compounds, therefore, may be less likely to deplete the levels of glutathione in a patient's cells, and thereby compromise their anti-oxidant defences, than the equivalent cyclohex-2-en-1-one derivatives. Without wishing to be bound by theory, this may explain why some compounds in accordance with the invention that include one or more —SR group have significantly enhanced therapeutic indices, in addition to enhanced or reduced water solubility and enhanced or reduced lipophilicity.

Without again wishing to be bound by theory, it is considered that compounds in accordance with the present invention, wherein the carbon atom in the 3 position in their cyclohexanone rings carries an —SR group, enjoy their enhanced properties partially because they can act as pro-drugs for the equivalent cyclohex-2-en-1-ones, in the sense that it is thought that they are converted into the latter in vivo. In this regard, it is considered that, before it is cleaved, the group —SR renders these compounds in accordance with the invention more suited to a chosen mode of administration (e.g. oral or topical to the skin) and that in vivo cleavage of the —SR group releases, via a reverse Michael reaction, the more potent cyclohex-2-en-1-one equivalent.

Thus, in embodiments, compounds of formula II in accordance with the invention are transformable into equivalent cyclohex-2-en-1-one derivatives of formula I by a reverse Michael reaction, or are pro-drugs for such equivalents.

In further preferred embodiments, the group —SR is an S-cysteinyl or a substituted S-cysteinyl group. In the context of this application, a substituted or unsubstituted S-cysteinyl group comprises a cysteinyl moiety that is bound to the ring via its sulphur atom, with the ring replacing the hydrogen atom that is bound to the equivalent sulphur atom in cysteine. Preferred substituted S-cysteinyl groups include di- and tripeptide groups that include an S-cysteinyl moiety, such as S-glutathionyl, S-cysteinyl ester and other like groups, including N-tert-butoxycarbonyl S-cysteinyl and N-tert-butoxycarbonyl S-cysteinyl ester (e.g. methyl and ethyl) groups.

Without once again wishing to be bound by theory, it is considered that compounds in accordance with these latter embodiments of the invention are also capable of providing a secondary therapeutic effect resulting from their incorporation of a substituted or unsubstituted cysteinyl moiety. For example, when acting as pro-drugs in the aforementioned manner, such compounds may be capable of delivering both the equivalent cyclohex-2-en-1-one derivative and the reduced form of the substituted or unsubstituted cysteinyl moiety to target cells in a patient's body, where both may exert their therapeutic effects. The therapeutic effect exerted by the reduced form of the substituted or unsubstituted cysteinyl moiety can be the prevention of glutathione depletion, especially when the reduced moiety is glutathione, an analogue or precursor. For example, the reduced, substituted or unsubstituted cysteinyl moiety may compete with native glutathione, to reduce the amount of the latter that is bound by the cyclohex-2-en-1-one derivative (formed after in vivo cleavage) or a metabolite, or it may replace or lead to the replacement of glutathione bound by the derivative or a metabolite. Such activity is thought to contribute significantly to reducing the toxicity of the inventive compounds and, hence, to the increased therapeutic indices enjoyed by these compounds, in comparison to the equivalent cyclohex-2-en-1-ones.

Compounds in accordance with the invention preferably are capable of one or more of the following:
 (a) activating HSF
 (b) inhibiting NF-κB
 (c) inhibiting the replication of HSV-1
 (d) inhibiting the replication of Sendai virus
 (e) inducing apoptosis in cancer cell lines
 (f) showing anti-angiogenic activity.

A skilled person can readily assay for the above activities and examples of suitable assays for apoptosis are set out in Examples 2 and 3 below.

Compounds that have greater activity in at least one of the foregoing respects than cyclopent-2-en-1-one (at least at certain concentrations) represent preferred embodiments of the invention; those that enjoy such activity at a concentration within the range of 1-200 µM, or over the whole or a part of said range, being particularly preferred. Preferably, compounds in accordance with the invention have a level of activity in at least one of the foregoing respects that is at least twice the level of cyclopent-2-en-1-one. More preferably, it is at least 10 times that of cyclopent-2-en-1-one.

Activity in one of the above respects is indicative of a compound's capacity to be pharmaceutically active. Accordingly, in a yet further aspect, the present invention provides a compound in accordance with the invention for use in medicine (including veterinary medicine). Preferred such uses include the treatment of the human or animal body by therapy and diagnostic methods practiced upon the human or animal body. The treatment may be prophylactic or may be in respect of an existing condition. Therapeutic (including prophylactic) and diagnostic methods, involving the use of a compound in accordance with the invention, are also within the remit of the invention. The use of such compounds for the manufacture of medicaments for use in therapeutic or diagnostic methods to be practiced on the human or animal body, lie within the scope of a further aspect of the invention.

The preferred uses for compounds in accordance with the invention include the treatment of disorders which can be treated in a host by the activation of a heat shock transcription factor (e.g. HSF1), by the induction of heat shock proteins (e.g. HSP70), and/or by the inhibition of NF-κB. Certain preferred compounds in accordance with the invention can be used in therapeutic applications that involve activating HSF and inhibiting the activity of NF-κB.

Thus, in accordance with the invention, compounds in accordance with the invention can be used to treat diseases or conditions in which such activity is indicated or can be of advantage. They can also be used in the manufacture of medicaments for use in such treatments. The preferred therapeutic and diagnostic applications for the inventive compounds are discussed in detail below.

In a further embodiment of the present invention, there is provided a method of changing the lipophilicity, water solubility and/or therapeutic index of a pharmaceutically active compound of formula I, as defined above, said method comprising forming an adduct of said compound of formula I and a thiol of the formula R—SH, wherein R is as herein before defined and the adduct is a compound of formula II, as defined above. In an embodiment, this method involves decreasing the lipophilicity and/or increasing the water solubility and/or the therapeutic index of the pharmaceutically active compound of formula I. In an alternative embodiment, the method involves decreasing the water solubility and/or increasing the lipophilicity and/or the therapeutic index of the pharmaceutically active compound of formula I.

The adduct may act as a pro-drug in the manner discussed above, or it may be pharmaceutically active in its own right.

In preferred embodiments of this method, the adduct is formed via a Michael reaction between the unsaturated compound of formula I and the thiol. A preferred method of forming the adduct is described in the examples that follow.

A further —SR group can, optionally, be present or be added into a side chain bound to the cyclohexanone ring of compounds of formula II.

In a further aspect, the present invention provides an adduct as herein before defined, prepared or preparable by a method in accordance with the invention.

For the avoidance of doubt, it is confirmed that the term "alkenyl" denotes a group with one or more double bonds in its carbon skeleton and the term "alkynyl" denotes a group with one or more triple bonds in its carbon skeleton. It should also be understood that, for the purposes of this specification, alkynyl groups may include both double and single bonds in their carbon skeletons. Unless otherwise specified, groups referred to in this specification as alkyl, alkenyl or alkynyl groups can be straight chained or branched, or be or include cyclic groups. However, unless the contrary is indicated, they are preferably straight chained or branched.

Medical Uses for Compounds in Accordance with the Invention

The preferred uses for compounds in accordance with the invention include the treatment of disorders which can be treated in a host by the activation of a heat shock transcription factor (e.g. HSF1), by the induction of heat shock proteins (e.g. HSP70), and/or by the inhibition of NF-κB.

Certain preferred compounds in accordance with the invention can be used in therapeutic applications that involve activating HSF and inhibiting the activity of NF-κB. Thus, in accordance with the invention, such compounds can be used to treat diseases or conditions in which such activity is indicated or can be of advantage. They can also be used in the manufacture of medicaments for use in such treatments. Preferred therapeutic and diagnostic applications for such compounds are discussed below.

It should be appreciated that certain compounds in accordance with the invention do not exhibit activity in all of the respects discussed above. Such compounds, therefore, may only find use in those of the therapeutic and diagnostic applications detailed below where their properties are indicative of potential usefulness.

It should be appreciated that certain disorders, e.g. cancers, may be mediated by viruses and by non-viral factors. In the absence of any indication to the contrary, treatment of any given disorder is covered whether or not the disorder is mediated by viruses. It should also be appreciated that there is some overlap between the various categories of treatment discussed, i.e. the categories are not intended to be mutually exclusive.

1. Treatment of Viral-Mediated Disorders

NF-κB is implicated in the pathogenesis of certain viral infections. It is known that heat shock proteins (e.g. HSP70) can offer protection against the pathogenesis of viral infection. Compounds in accordance with the invention may be active in reducing the replication of viruses.

Compounds in accordance with the invention may be useful in treating viral-mediated disorders. These include disorders mediated by RNA viruses, as well as disorders mediated by DNA viruses.

Examples of viral disorders that may be treated using compounds in accordance with the invention include the following.

Diseases caused by or associated with members of the Adenoviridae family, including (but not limited to): diarrhea or intussusception caused by or associated with enteric adenoviruses; upper or lower respiratory tract infections (including the common cold or pneumonia) caused by or associated with respiratory adenoviruses; conjunctivitis, keratitis or trachoma caused by or associated with adenovirus infection of the eye; tonsillar or kidney infections caused by or associated with adenoviruses.

Diseases caused by or associated with members of the Arenaviridae family, including (but not limited to): Lassa fever caused by Lassa fever virus; meningitis caused by or associated with lymphocytic choriomeningitis virus; hemorrhagic fevers including (but not limited to) those caused by Machupo virus, Junin virus, Sabia virus, Guanarito virus or Tacaribe virus.

Diseases caused by or associated with members of the Astroviridae family, including (but not limited to): diarrhea caused by or associated with astroviruses.

Diseases caused by or associated with members of the Bunyaviridae family, including (but not limited to): hemorrhagic fever with renal syndrome, hantavirus pulmonary syndrome, or other diseases caused by or associated with hantaviruses including (but not limited to) Hantaan virus, Puumala virus, Seoul virus, Dobrava virus, Sin Nombre virus, bayou virus, Black Creek canal virus, New York 1 virus, Monogahela virus, Andes virus, and Laguna Negra virus; arbovirus infections including (but not limited to) La Crosse encephalitis, California encephalitis, or other bunyavirus infections; Rift Valley fever, sandfly fever, Uukuniemi or other arbovirus infections associated with phleboviruses; Crimean-Congo hemorrhagic fever or other infections caused by Nairoviruses.

Diseases caused by or associated with members of the Caliciviridae family or related agents, including (but not limited to): hepatitis caused by or associated with hepatitis E virus, diarrhea caused by or associated with caliciviruses or small round structured viruses.

Diseases caused by or associated with members of the Coronaviridae family, including (but not limited to): lower or upper respiratory tract infections (including the common cold) caused by or associated with coronaviruses; diarrhea, enterocolitis or gastroenteritis caused by or associated with coronaviruses or toroviruses.

Diseases caused by or associated with members of the Filoviridae family, including (but not limited to): hemorrhagic fevers caused by Ebola or Marburg viruses.

Diseases caused by or associated with members of the Flaviviridae family, including (but not limited to): arbovirus infections, fevers or encephalitides including (but not limited to) yellow fever, Kyansur Forest disease, Omsk hemorrhagic fever, other tick-borne encephalitis infections, Rocio, Japanese encephalitis, St. Louis encephalitis, West Nile virus infection, Murray Valley encephalitis, Dengue fever, or Dengue hemorrhagic fever caused by or associated with flaviviruses; hepatitis caused by or associated with hepatitis C virus.

Diseases caused by or associated with members of the Hepadnaviridae family, including (but not limited to): hepatitis caused by or associated with hepatitis B virus.

Diseases caused by or associated with members of the Her esviridae family, including (but not limited to): orolabial herpes, genital herpes, herpetic dermatitis, herpetic whitlow, zosteriform herpes simplex, ocular disease, encephalitis or neonatal herpes caused by or associated with herpes simplex viruses types 1 or 2; chickenpox, shingles, zoster-associated pain, pneumonia, encephalitis, fetal infection or retinal necrosis caused by or associated with varicella-zoster virus; transplant rejection, congenital infection, infectious mononucleosis, retinitis or other diseases of the immunocompromised caused by or associated with cytomegalovirus; infectious mononucleosis, lymphomas, carcinomas or other cancers caused by or associated with Epstein-Barr virus; exanthem subitum, roseola infantum, pneumonitis or hepatitis caused by or associated with human herpes viruses 6 or 7; Kaposi's sarcoma or other neoplastic disease caused by or associated with human herpes virus 8 (KSV).

Diseases caused by or associated with members of the Orthomyxoviridae family, including (but not limited to): influenza, pneumonia, other respiratory infections, myositis, myoglobinuria, or Reye's syndrome caused by or associated with influenza viruses A, B or C.

Diseases caused by or associated with members of the Papovaviridae family, including (but not limited to): papillomas, comdylomas, neoplasias and carcinomas caused by or associated with papillomaviruses; diseases caused by BKV or JCV viruses; progressive multifocal leukoencephalopathy caused by polyomaviruses.

Diseases caused by or associated with members of the Parpoviridae family, including (but not limited to): anemia, fever, fetal infection or hepatitis caused by or associated with parvorvirus B19.

Diseases caused by or associated with members of the Paramyxoviridae family, including (but not limited to): pneumonia, bronchiolitis, tracheobronchitis or croup caused by or associated with parainfluenza viruses; bronchiolitis or pneumonia caused by or associated with respiratory syncytial virus; encephalitis, measles or complications of measles including (but not limited to) pneumonia or sub-acute sclerosing panencephalitis (SSPE) caused by or associated with measles virus; mumps or complications of mumps including (but not limited to) orchitis or pancreatitis caused by or associated with mumps virus.

Diseases caused by or associated with members of the Picornaviridae family, including (but not limited to): hepatitis caused by or associated with hepatitis A virus; upper respiratory tract infections (including the common cold) caused by or associated with rhinoviruses or other respiratory picornaviruses; poliomyelitis caused by polioviruses; Bornholm disease, encephalitis, meningitis, herpangina, myocarditis, neonatal disease, pancreatitis, fever, conjunctivitis, chronic fatigue syndrome (ME) or hand, foot and mouth disease caused by coxsackieviruses or enteroviruses.

Diseases caused by or associated with members of the Poxviridae family, including (but not limited to): smallpox caused by smallpox virus; human forms of monkeypox or cowpox virus infections; infections with vaccinia virus including (but not limited to) complications of vaccination; orf or paravaccinia caused by parapoxviruses; molluscum contagiosum caused by molluscipoxviruses; infections with Tanapox virus.

Diseases caused by or associated with members of the Reoviridae family, including (but not limited to): diarrhea caused by or associated with rotaviruses.

Diseases caused by or associated with members of the Retroviridae family, including (but not limited to): acquired immune deficiency syndrome and associated disorders caused by or associated with human immunodeficiency virus (HIV); leukaemias, lymphomas, or myelopathies caused by or associated with HTLV viruses.

Diseases caused by or associated with members of the Rhabdoviridae family, including (but not limited to): rabies caused by rabies virus; other lyssavirus diseases including (but not limited to) those caused by Duvenhage or Mokola viruses.

Diseases caused by or associated with members of the Togaviridae family, including (but not limited to): rubella or congenital rubella syndrome caused by rubella virus; fever or encephalitis caused by eastern equine encephalitis virus, Venezuelan equine encephalitis virus, western equine encephalitis virus, Everglades virus or Semliki Forest virus; fever, rash, polyarthritis, myalgia or arthralgia caused by Sindbis virus, Ockelbo virus, Ross River virus, Barmah Forest virus, Chikungunya virus, O'nyong-nyong virus, Mayaro virus or Igo Ora virus.

Diseases caused by or associated with viroid-like agents, including (but not limited to): hepatitis caused by or associated with the delta agent (HDV).

Diseases caused by or associated with prions, including (but not limited to): Creutzfeld-Jakob disease (CJD), new variant CJD, GSS, and fatal familial insomnia.

Compounds of the present invention may be particularly useful in treating viral and other disorders affecting aquatic organisms (e.g. fish, crustaceans, etc.). Such disorders include disorders mediated by the snout ulcer virus, by the iridovirus, by the lymphocystis disease virus, etc.

Compounds in accordance with the invention may therefore be used in aquaculture. They may be used in food for aquatic organisms. Such food is within the scope of the present invention. It will generally be sold in sealed containers and labelled appropriately (e.g. as fish food, food for crustaceans, food for aquatic organisms, etc.). Alternatively, compounds in accordance with the invention may be used for water treatment or for direct application to aquatic organisms. Such compounds do not therefore need to be present in foodstuffs in order to be useful in aquaculture.

2. Treatment of Bacterial-Mediated Disorders

NF-κB is activated in response to bacterial infections.

Compounds in accordance with the invention can be useful in treating disorders arising from such infections, e.g. in treating NF-κB stimulated inflammation. Most commonly this will arise due to infection with gram negative bacteria. However it may also arise due to infection with gram positive bacteria (e.g. *S. aureus*).

3. Treatment of Disorders Mediated by Radiation

NF-κB is activated in response to radiation (e.g. UV-radiation).

Compounds in accordance with the invention can be useful in treating disorders mediated by radiation. Such disorders include cell and tissue trauma, cell and tissue ageing and cancer (e.g. skin cancer).

4. Treatment of Inflammation and of Disorders of the Immune System

NF-κB is activated in response to inflammatory cytokines. It is believed to be an early mediator of the immune and inflammatory responses.

Compounds in accordance with the invention can be useful in treating immune disorders (e.g. auto-immune disorders) and in treating inflammatory disorders. Examples of specific inflammatory disorders and disorders of the immune system that may be treated with such compounds include psoriasis, rheumatoid arthritis, multiple sclerosis, adult respiratory distress syndrome, hepatitis and/or cirrhosis, vascular inflammation (including lupus erythematosis disseminata), and inflammatory disorders of the gastro-intestinal tract (e.g. ulcers). Preferred amongst these uses is the treatment of psoriasis, particularly by the topical application of a compound in accordance with the invention formulated in a suitable composition, such as a cream, ointment or the like.

5. Treatment of Ischemia and Arteriosclerosis

NF-κB has been implicated in the pathogenesis of ischemia and arteriosclerosis. Compounds in accordance with the invention are therefore useful in treating such disorders, including reperfusion damage (e.g. in the heart or brain) and cardiac hypertrophy.

6. Treatment of Disorders Involving Cell Proliferation

NF-κB is implicated in cell proliferation.

Compounds in accordance with the invention can be useful as anti-proliferatives. They are therefore useful in treating inflammatory granulomas, neointimal proliferation in arterial and venous restenosis, and cancers.

Compounds in accordance with the invention can be useful in treating a disorder involving cell proliferation, including psoriasis, acne vulgaris, acne rosacea, actinic keratosis, solar keratosis, squamous carcinoma in situ, ichthyosis, hyperkeratosis, a disorder of keratinization such as Dariers disease, palmoplantar keratoderma, pityriasis rubra pilaris, epidermal naevoid syndrome, erythrokeratoderma variabilis, epidermolytic hyperkeratosis, non-bullous ichthyosiform erythroderma, cutaneous lupus erythematosus, lichen planus, a cancer in which NF-κB is constitutively activated, glioma, head and neck cancer, lung cancer, colon cancer, pancreatic cancer, neuroblastoma, hepatocarcinoma, and a disorder of angiogenesis.

Compounds in accordance with the invention can be particularly useful in treating cancers, including lymphomas, melanomas, leukemias, sarcomas, carcinomas, breast cancers (especially late stage breast cancers and estrogen receptor negative breast cancers), prostate cancers, liver cancers, multiple myelomas and B-cell malignancies, and including cancers which are resistant to conventional chemotherapy and/or radiotherapy.

When compounds in accordance with the invention are used for the treatment of cancer, they may be administered in combination with other chemotherapeutic agents or in combination with radiotherapy. Such combined administration can involve the simultaneous, separate or sequential administration of the compounds in accordance with the invention and the other chemotherapeutic agents or radiotherapy. Suitable other chemotherapeutic agents include, but are not limited to, Paclitaxel, Cisplatin, Vinblastine, Etoposide and Doxorubicin.

7. Treatment of Disorders Involving Damage to or Killing of Cells

Heat shock proteins are known to provide a cytoprotective effect.

Compounds in accordance with the invention can be useful in treating disorders involving damage to or killing of cells.

These disorders include chemical toxicity (e.g. due to ingestion of toxins, such as paraquat, or to overdosing with medicaments, such as paracetamol), oxidative cell damage, cell and tissue ageing, trauma, hepatitis, diabetes and the effect of burns. The inventive compounds, also, can be used to combat the effects of ageing in a human or animal, and to promote wound healing.

Other conditions of this general nature, that can be treated using compounds of the present invention, include oxidative stress and degenerative diseases, especially neuro-degenerative diseases such as BSE, new variant CJD and Alzheimer's disease.

8. Other Treatments

Cyclopentenone prostaglandins are of known utility in stimulating peroxisome proliferator activated receptors (PPARs). Compounds in accordance with the invention, thus, can be useful in treating diabetes (including complications arising therefrom). Such compounds can also be used in the treatment of disorders in which calcium loss or deficiency is implicated or involved (including bone disorders, disorders of bone growth, bone fractures, osteoporosis, skeletal disorders, dental disorders, developmental disorders, etc.).

Routes of Administration for Compounds in Accordance with the Invention

A medicament will usually be supplied as part of a pharmaceutical composition, which may include a pharmaceutically acceptable carrier. This pharmaceutical composition will generally be provided in a sterile form. It may be provided in unit dosage form. It will generally be provided in a sealed container, and can be provided as part of a kit. Such a kit is within the scope of the present invention. It would normally (although not necessarily) include instructions for use. A plurality of unit dosage forms may be provided.

Pharmaceutical compositions within the scope of the present invention may include one or more of the following: preserving agents, solubilising agents, stabilising agents, wetting agents, emulsifiers, sweeteners, colourants, odourants, salts (compounds of the present invention may themselves be provided in the form of a pharmaceutically acceptable salt, as explained in greater detail below), buffers, coating agents or anti-oxidants. They may also contain other therapeutically active agents in addition to a compound of the present invention.

Compounds of the present invention may themselves be provided in any suitable form, i.e. they may be used as such or may be used in the form of a pharmaceutically effective derivative. For example they may be used in the form of a pharmaceutically acceptable salt or hydrate. Pharmaceutically acceptable salts include alkali metal salts (e.g. sodium or potassium salts), alkaline earth metal salts (e.g. calcium or magnesium salts), aluminium salts, zinc salts, ammonium salts (e.g. tetra-alkyl ammonium salts), etc. Inorganic acid addition salts (e.g. hydrochlorides, sulphates, or phosphates) or organic acid addition salts (e.g. citrates, maleates, fumarates, succinates, lactates, propionates or tartrates) may be used.

Pharmaceutical compositions of the present invention may be provided in controlled release form. This can be achieved by providing a pharmaceutically active agent in association with a substance that degrades under physiological conditions in a predetermined manner. Degradation may be enzymatic or may be pH-dependent.

Pharmaceutical compositions may be designed to pass across the blood brain barrier (BBB). For example, a carrier such as a fatty acid, inositol or cholesterol may be selected that is able to penetrate the BBB. The carrier may be a substance that enters the brain through a specific transport system in brain endothelial cells, such as insulin-like growth factor I or II. The carrier may be coupled to the active agent or may contain/be in admixture with the active agent. Liposomes can be used to cross the BBB. WO91/04014 describes a liposome delivery system in which an active agent can be encapsulated/embedded and in which molecules that are normally transported across the BBB (e.g. insulin or insulin-like growth factor I or II) are present on the liposome outer surface. Liposome delivery systems are also discussed in U.S. Pat. No. 4,704,355.

A pharmaceutical composition within the scope of the present invention may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) routes. Such a composition may be prepared by any method known in the art of pharmacy, for example by admixing one or more active ingredients with a suitable carrier. In preferred embodiments, compounds in accordance with the invention are formulated into oral dosage forms and, therefore, are preferably provided in tablet or capsule form.

Different drug delivery systems can be used to administer pharmaceutical compositions of the present invention, depending upon the desired route of administration. Drug delivery systems are described, for example, by Langer (Science 249, 1527-1533 (1991)) and Illum and Davis (Current Opinions in Biotechnology 2m 254-259 (1991)). Different routes of administration for drug delivery will now be considered in greater detail.

(i) Oral Administration

Pharmaceutical compositions adapted for oral administration may be provided as capsules or tablets; as powders or granules; as solutions, syrups or suspensions (in aqueous or non-aqueous liquids); as edible foams or whips; or as emulsions. Tablets or hard gelatine capsules may comprise lactose, maize starch or derivatives thereof, stearic acid or salts thereof. Soft gelatine capsules may comprise vegetable oils, waxes, fats, semi-solid, or liquid polyols etc. Solutions and syrups may comprise water, polyols and sugars. For the preparation of suspensions, oils (e.g. vegetable oils) may be used to provide oil-in-water or water-in-oil suspensions.

An active agent intended for oral administration may be coated with or admixed with a material that delays integration and/or absorption of the active agent in the gastrointestinal tract (e.g. glyceryl monostearate or glyceryl distearate may be used).

Thus, the sustained release of an active agent may be achieved over many hours and, if necessary, the active agent can be protected from being degraded within the stomach. Pharmaceutical compositions for oral administration may be formulated to facilitate release of an active agent at a particular gastrointestinal location due to specific pH or enzymatic conditions.

(ii) Transdermal Administration

Pharmaceutical compositions adapted for transdermal administration may be provided as discrete patches intended to remain in intimate contact with the epidermis of the recipient for a prolonged period of time. For example, the active ingredient may be delivered from the patch by iontophoresis. (Iontophoresis is described in *Pharmaceutical Research*, 3(6):318, 1986).

(iii) Topical Administration

Pharmaceutical compositions adapted for topical administration may be provided as ointments, creams, suspensions, lotions, powders, solutions, pastes, gels, sprays, aerosols or oils. For topical administration to the skin, mouth, eye or other external tissues, a topical ointment or cream is preferably used. When formulated in an ointment, the active ingredient may be employed with either a paraffinic or a water-miscible ointment base. Alternatively, the active ingredient may be formulated in a cream with an oil-in-water base or a water-in-oil base. Pharmaceutical compositions adapted for topical administration to the eye include eye drops. Here the active ingredient can be dissolved or suspended in a suitable carrier, e.g. in an aqueous solvent. Pharmaceutical compositions adapted for topical administration in the mouth include lozenges, pastilles and mouthwashes.

(iv) Rectal Administration

Pharmaceutical compositions adapted for rectal administration may be provided as suppositories or enemas.

(v) Nasal Administration

This includes not only administration to the nasal cavity, but also administration via the nasal cavity to another location, e.g. to the lungs.

Pharmaceutical compositions adapted for nasal administration may use solid carriers, e.g. powders (preferably having a particle size in the range of 20 to 500 microns). Powders can be administered in the manner in which snuff is taken, i.e. by rapid inhalation through the nose from a container of powder held close to the nose. Compositions adopted for nasal administration may alternatively use liquid carriers, e.g. include nasal sprays or nasal drops. These may comprise aqueous or oil solutions of the active ingredient.

Compositions for administration by inhalation may be supplied in specially adapted devices, e.g. in pressurised aerosols, nebulizers or insufflators. These devices can be constructed so as to provide predetermined dosages of the active ingredient.

(vi) Vaginal Administration

Pharmaceutical compositions adapted for vaginal administration may be provided as pessaries, tampons, creams, gels, pastes, foams or spray formulations.

(vii) Parenteral Administration

Pharmaceutical compositions adapted for parenteral administration include aqueous and non-aqueous sterile injectable solutions or suspensions. These may contain antioxidants, buffers, bacteriostats and solutes that render the compositions substantially isotonic with the blood of an intended recipient. Other components that may be present in such compositions include water, alcohols, polyols, glycerine and vegetable oils, for example. Compositions adapted for parenteral administration may be presented in unit-dose or multi-dose containers, for example sealed ampoules and vials, and may be stored in a freeze-dried (lyophilised) condition requiring only the addition of a sterile liquid carrier, e.g. sterile water for injections, immediately prior to use. Extemporaneous injection solutions and suspensions may be prepared from sterile powders, granules and tablets.

From the above description it will be appreciated that compositions of the present invention can be formulated in many different way.

Dosages

Dosages of a compound of the present invention can vary between wide limits, depending upon the nature of the treatment, the age and condition of the individual to be treated, etc. and a physician will ultimately determine appropriate dosages to be used.

However, without being bound by any particular dosages, a daily dosage of a compound of the present invention of from 10 g to 100 mg/kg body weight may be suitable.

More preferably the dosage is from 5 to 50 mg/kg body weight/day. The dosage may be repeated as often as appropriate. If side effects develop, the amount and/or frequency of the dosage can be reduced, in accordance with good clinical practice.

Research Uses

Compounds of the present invention are useful in research. For example, they can be used as research tools for the analysis of one or more of the following: HSF, NF-κB, the heat shock response, viral replication, viral-mediated disorders, bacterial-mediated disorders, disorders mediated by radiation (e.g. by UV-radiation), inflammatory disorders, disorders of the immune system, ischemia, arteriosclerosis, disorders involving cell proliferation (e.g. cancers), disorders involving damage to or killing of cells (e.g. oxidative cell damage), and diabetes.

Other Uses

Compounds of the present invention can also be useful in treating plant vital disorders. Given that the basic mechanisms of the heat shock response are believed to operate in a similar fashion in plants and animals and that it is reasonable to expect that direct antiviral effects will be produced by the compounds of invention in a similar fashion in plants and animals, the use of compounds of the present invention in treating viral infections of plants is within the scope of the present invention. These infections include, but are not limited to, infections by plants of geminiviruses, thabdoviruses, caulimoviruses, bromoviruses, tobramoviruses, potyviruses and potexviruses. The use of compounds of the present invention in treating infections by viroids (including, but not limited to, potato spindle turnout viroid, hop stunt viroid, and coconut cadang-cadang viroid) is also within the scope of the invention.

Compounds of the present invention may be particularly useful in treating viral and other disorders affecting aquatic organisms (e.g. fish, crustaceans, etc.). Such disorders include disorders mediated by the snout ulcer virus, iridovirus, lymphocystis disease virus, infectious salmon anaemia, nodaviruses etc.

Compounds of the present invention may therefore be used in aquaculture. They may be used in food for aquatic organisms. Such food is within the scope of the present invention. It will generally be sold in sealed containers and labelled appropriately (e.g. as fish food, food for crustaceans, food for aquatic organisms, etc.). Alternatively, compounds of the present invention may be used for water treatment or for direct application to aquatic organisms. Such compounds do not therefore need to be present in foodstuffs in order to be useful in aquaculture.

SYNTHETIC EXAMPLES

Cyclohexenones of formula I can be prepared using the following general method (general method A).

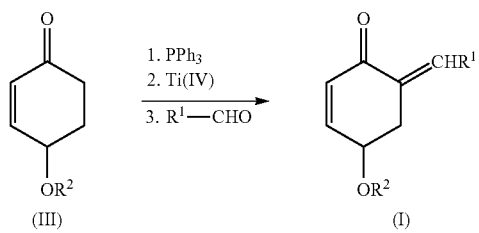

General Method A: Add triphenylphosphine (about 1 eq) to a stirred solution of cyclohexenone (III) (about 1 eq) in dichloromethane at room temperature under an inert atmosphere. Cool the mixture to about −50° C. Add titanium (IV) isopropoxide (about ½ eq) and then titanium (IV) chloride (about ½ eq) dropwise. Stir the mixture at about −50° C. for about 15 minutes, then add aldehyde $R^1$—CHO (about 3 eq) dropwise. Allow the mixture to warm to room temperature over about 15 hours. Add an aqueous solution of potassium carbonate (10%) and stir the biphasic mixture for about 90 minutes, filter through Celite® washing with dichloromethane and diethyl ether. Separate the organic phase and extract the aqueous phase with diethyl ether. Dry the combined organic extracts over magnesium sulphate and evaporate the solvent in vacuo. Purify the residue by flash chromatography over silica to afford cyclohexenone (I).

Cyclohexanones of formula II can be prepared from the equivalent cyclohexenones of formula I using the following general method (general method B).

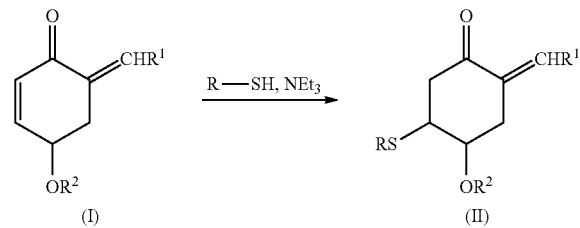

General Method B: To a solution of cyclohexenone (I) (about 1 eq) in anhydrous chloroform add a solution of thiol R—SH (about 1 eq) and triethylamine (cat.) in anhydrous chloroform at room temperature. Stir the reaction for about 18 hours under an inert atmosphere and then evaporate the solvent in vacuo. Purify the residue by flash chromatography over silica to afford cyclohexanone (II).

Example 1

Preparation of (R)-2-tert-Butoxycarbonylamino-3-[4E-benzylidene-2(tert-butyl-dimethylsilanyloxy)-5-oxo-cyclohexylsulfanyl]-propionic acid methyl ester (CTM-208)

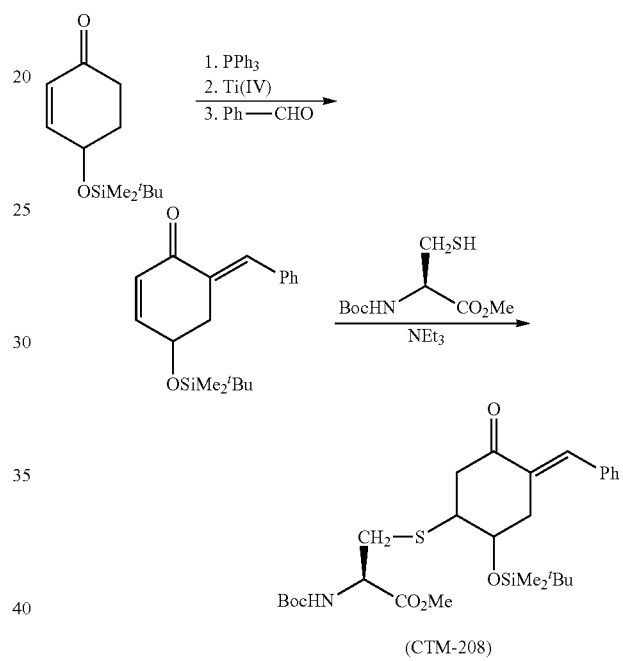

Following general method A, triphenylphosphine (225 mg, 0.86 mmol) was added to a stirred solution of 4-(tert-butyl-dimethylsilanyloxy)-cyclohex-2-enone (194 mg, 0.86 mmol) in dichloromethane (5 cm³) at room temperature under an atmosphere of argon. The mixture was cooled to −50° C.; titanium (IV) isopropoxide (0.13 cm³, 0.44 mmol) and then titanium (IV) chloride (47 μL, 0.43 mmol) were added dropwise. The mixture was stirred at −50° C. for 15 minutes, then benzaldehyde (0.26 cm³, 2.56 mmol) was added dropwise. The mixture was allowed to warm to room temperature over 15 hours. An aqueous solution of potassium carbonate (10%, 10 cm³) was added and the biphasic mixture stirred for 90 minutes, and filtered through Celite® washing with dichloromethane (10 cm³) and diethyl ether (10 cm³). The organic phase was separated and the aqueous phase was extracted with diethyl ether (4×10 cm³). The combined organic extracts were dried over magnesium sulphate and evaporated in vacuo. Flash chromatography gave 6E-benzylidene-4-(tert-butyl-dimethylsilanyloxy)-cyclohex-2-enone in 62% yield as a white solid, m.p. 40-42° C.

To a solution of this compound (100 mg) in anhydrous chloroform (1.0 cm³) was added a solution of Boc-cysteine methyl ester (60 mg) and triethylamine (3 drops) in anhydrous chloroform (1.5 cm³). The reaction was stirred for 18 hours under argon and then the solvent was evaporated in vacuo. The residue was purified by chromatography over silica to afford the title compound in 65% yield; 8H (250 MHz, CDCl$_3$) 0.13 (6H, s, Si$^t$Bu(CH$_3$)), 0.90 (9H, s, SiMe$_2$C (CH$_3$)$_3$), 1.50 (9H, s, OC(CH$_3$)$_3$), 2.40-3.40 (7H, m, 3×CH$_2$, SCH), 3.80 (3H, s, OCH$_3$), 4.10 (1H, M, OCH), 4.60 (1H, m, CH (Cys)), 5.05 (1H, d, NH), 7.30-7.50 (5H, m, ArH), 7.60 (1H, brd, C=CHAr).

In order to prepare enantiomers (CTM-208-2R,1'S,2'S) and (CTM-208-2R,1'R,2'R), the above procedure can be followed using (−)-(S)- or (+)-(R)-4-(tert-butyl-dimethylsilanyloxy)-cyclohex-2-enone respectively.

BIOLOGICAL EXAMPLES

Activity of Compounds in Accordance with the Invention

Preferred compounds of the present invention have activity in one or more of the assays described in Examples 2 and 3.

Example 2

Cell Culture and Treatments. Human breast cancer MDA-MB-231, human melanoma SK-MEL-28, and human Burkitt lymphoma HS-Sultan cell lines, obtained from ATCC (Manassas, Va.), were grown at 37° C. in 5% CO$_2$ and 95% humidified air in cell culture medium containing 10% fetal calf serum, 2 mM glutamine and antibiotics (100 µM penicillin and 0.1 mg/ml streptomycin) (Life Technologies, Inc.). Each compound to be assayed was dissolved in absolute ethanol and diluted in the culture medium immediately before use. Control cells received the same amount of ethanol diluent. Cells were incubated with the assay compound or control diluent for 8 hours, unless indicated otherwise. Cell viability was determined by vital-dye exclusion assay (Trypan blue, 0.1%).

Flow Cytometry. For Annexin V staining, cells were washed once with PBS and resuspended in staining buffer (10 mM HEPES pH 7.4, 140 mM NaCl, 2.5 mM CaCl) with 5 ml of AnnexinV-PI (AnnexinV-FITC, Becton-Dickinson). After 15 minutes of incubation in the dark, cells were directly analyzed in a FACScan (Becton-Dickinson). Cells were evaluated with CellQuest Program (Becton-Dickinson). Data were plotted using a histogram algorithm, in which the intensities of AnnexinV-positive cells were represented as percent of untreated control. Exemplary data obtained from human Burkitt lymphoma HS-Sultan cells and human melanoma SK-MEL-28 cells (24 hour incubation for SK-MEL-28 cells) are provided in FIGS. 1 and 2, respectively. The data show CTM-208 to be a potent inducer of apoptosis in these cells in comparison to 15d-PGJ$_2$ and the chemotherapeutic agents tested (Cisplatin, Etoposide and Vinblastine).

DNA Fragmentation. Cytoplasmic histone-bound DNA fragments (mono- and oligo-nucleosomes) generated during apoptosis were measured by Cell-Death-Detection ELISA kit (Roche Diagnostics, Mannheim, Germany), according to the manufacturer's instructions. Histone-associated DNA fragments were quantified spectrophotometrically using antibodies against DNA and histones in a colorimetric assay. Enrichment in cytoplasmic nucleosomes was expressed as fold-induction of levels in untreated controls. Exemplary data using human breast cancer MDA-MB-231 cells (48 hour incubation) are provided in FIG. 3. As the data show, treatment of the cells with CTM-208 induced a dramatic dose-dependent increase of apoptosis that was significantly more than that seen with the chemotherapeutic agent, Paclitaxel. At 5 µM CTM-208, apoptosis was increased more than 35-fold over the untreated control. Further exemplary data using human melanoma SK-MEL-28 cells (48 hour incubation) are provided in FIG. 4.

Electrophoretic Mobility Shift Assay (EMSA). For nuclear extract preparation, cells (2×10$^6$ cells/sample) were lysed in hypotonic lysis buffer (10 mM NaCl, 3 mM MgCl$_2$, 10 mM Tris-HCl pH 7.8, 0.5% NP40, 1 mM DTT) and then in high-salt extraction buffer (50 mM Tris-HCl, 400 mM NaCl, 1 mM EDTA, 1 mM EGTA, 1% Triton, 0.5% NP-40, 10% glycerol, 1 mM DTT, 1 mM PMSF, 0.5 µg/ml leupeptin, 0.7 µg/ml pepstatin, 0.2% aprotinin). Equal amounts of protein (6 µg/sample) were incubated with $^{32}$P-labeled κB-DNA probe (11) followed by analysis of DNA-binding activity by EMSA. Binding reactions were performed as described (11). Complexes were analyzed by nondenaturing 4% polyacrylamide gel electrophoresis. Specificity of protein-DNA complexes was verified by immunoreactivity with polyclonal antibodies specific for the NF-κB subunit, p65/RelA. Quantitative evaluation of NF-κB-κB complex formation was determined by Typhoon-8600 Imager (Molecular Dynamics), using ImageQuant software (MDP analysis). Exemplary data from human Burkitt lymphoma HS-Sultan cells are provided in FIGS. 5 to 7. FIGS. 5 and 6 show CTM-208 to be a potent inhibitor of the constitutively high levels of NF-κB DNA-binding activity expressed by Burkitt lymphoma cells. As FIG. 6 shows, CTM-208 was effective at submicromolar concentrations with an IC$_{50}$ of 0.2 µM. In a parallel experiment on the same cells, using Annexin V-PI staining, CTM-208 was shown to be a potent inducer of apoptosis, starting to be effective at a concentration of 0.1 µM (FIG. 7). An 8 hour treatment with 0.5 µM CTM-208 induced approximately 90% apoptosis.

Example 3

Cell Lines and Treatments. Human keratinocytes (HaCaT) were grown routinely in DMEM supplemented with 10% FBS and 2 mM L-glutamine at 37° C. in a 5% CO$_2$ humidified atmosphere. Human umbilical vein endothelial cells (HU-VEC), obtained from Clonetics (San Diego, Calif., USA), were cultured in EGM medium (Clonetics, San Diego, Calif., USA) supplemented with 2% FBS, 10 mg/ml hEGF, 1 mg/ml hydrocortisone, 50 mg/ml gentamicin, 3 mg/ml BBE (bovine brain extract) at 37° C. in a 5% CO$_2$ humidified atmosphere.

Compounds. CTM-208 was dissolved in absolute ethanol or DMSO (0.1 M stock solution), stored at −20° C., and diluted in the culture medium immediately before use. Control cells received the same amount of DMSO diluent that had no effect on cell proliferation at the concentrations tested. Methotrexate was dissolved in DMSO. Dimethylfumarate was dissolved in absolute ethanol.

Cell Proliferation Assay. HaCaT cells (2.5×10$^4$ cells/well) were seeded in 24-well plates. After 24 hours, the medium was removed and the test compounds were added at different concentrations. At 48 hours after the addition of the compounds, cell proliferation was determined by counting the number of viable cells in a hemocytometer. Cell viability was determined by the Trypan blue vital dye exclusion technique. IC$_{50}$ values on the increase in the number of cells over the number of seeded cells were calculated at 48 hours after treatment.

DNA synthesis. HUVEC cells (5×10$^3$ cells/well) were seeded in 96-well plates. After 24 hours, the medium was removed and the test compounds were added at different concentrations. DNA synthesis was evaluated by incorporation of 5-bromo-2-deoxy-uridine (BrdU) into cellular DNA 48 hours after the addition of the compounds. The amount of BrdU integrated into DNA was evaluated by using a monoclonal antibody against BrdU (cell proliferation ELISA colorimetric assay, Roche). Absorbance (l: 405 nm) was measured using a Victor microtiter plate reader (Wallac), and data were analyzed using the Allfit program.

Electrophoretic Mobility Shift Assay (EMSA). For nuclear extract preparation, cells ($2\times10^6$ cells/sample) were lysed in hypotonic lysis buffer (10 mM NaCl, 3 mM $MgCl_2$, 10 mM Tris-HCl pH 7.8, 0.5% NP40, 1 mM DTT) and then in high-salt extraction buffer (50 mM Tris-HCl, 400 mM NaCl, 1 mM EDTA, 1 mM EGTA, 1% Triton, 0.5% NP-40, 10% glycerol, 1 mM DTT, 1 mM PMSF, 0.5 µg/ml leupeptin, 0.7 µg/ml pepstatin, 0.2% aprotinin). Equal amounts of protein (6 µg/sample) were incubated with $^{32}P$-labeled κB-DNA probe followed by analysis of DNA-binding activity by EMSA. Binding reactions were performed as described (11). Complexes were analyzed by nondenaturing 4% polyacrylamide gel electrophoresis. Specificity of protein-DNA complexes was verified by immunoreactivity with polyclonal antibodies specific for the NF-κB subunit, p65/RelA. Quantitative evaluation of NF-κB-κB complex formation was determined by Typhoon-8600 Imager (Molecular Dynamics), using ImageQuant software (MDP analysis). Detection of HSF was performed by EMSA (methods as described above), using a $^{32}P$-labeled HSE-DNA probe to detect the HSF-HSE complexes.

Effect of CTM-208 on human keratinocyte proliferation. Human keratinocytes (HaCaT) were seeded in 24-well plates at a concentration of $2.5\times10^4$ cells per well. After 24 hours, cells were treated with different concentrations of CTM-208 or DMSO diluent, or with the anti-psoriatic drugs dimethylfumarate and methotrexate. At 48 hours after the addition of the compounds, cell proliferation was determined by counting the number of viable cells in a hemocytometer. Each concentration of each compound was tested in duplicate samples. Results shown in Table 1 demonstrate that CTM-208 is a potent inhibitor of HaCaT cell proliferation, with an $IC_{50}$ of 2 µM. CTM-208 was found to be much more effective than the anti-psoriatic drug dimethylfumarate, which inhibited HaCaT cell proliferation with an $IC_{50}$ of 50 µM (Table 1).

TABLE 1

| human keratinocytes | |
|---|---|
| Compounds | $IC_{50}$ |
| CTM-208 | 2 µM |
| Methotrexate | <0.1 µM |
| Dimethylfumarate | 50 µM |

Effect of CTM-208 on human endothelial cell proliferation. Human endothelial cells (HUVEC) were seeded in 96-well plates at a concentration of $5\times10^3$ cells per well. After 24 hours, cells were treated with different concentrations of CTM-208. At 48 hours after the addition of the compounds, DNA synthesis was evaluated by incorporation of 5-bromo-2-deoxy-uridine (BrdU) into cellular DNA. The amount of BrdU integrated into DNA was evaluated by using the cell proliferation ELISA colorimetric assay. Each concentration was tested in duplicate samples. Results shown in Table 2 demonstrate that CTM-208 is a potent inhibitor of endothelial cell proliferation, with an $IC_{50}$ of 1.6 µM.

TABLE 2

| human endothelial cells | |
|---|---|
| Compounds | $IC_{50}$ |
| CTM-208 | 1.6 µM |

Effect of CTM208 on NF-κB binding activity and HSF induction. The effect of CTM-208 on the DNA-binding activity of NF-κB in human keratinocytes is shown in Table 3. The results show that CTM-208 is a potent inhibitor of NF-κB-DNA binding activity, with activity equivalent to that of the anti-psoriatic drug dimethylfumarate and greater than that of methotrexate. Similar activity is also observed in endothelial cells (Table 4). CTM-208 is also capable of inducing HSF in both human keratinocytes (Table 3) and endothelial cells (Table 4). These data demonstrate that CTM-208 has anti-inflammatory activity, acting via the induction of two separate pathways, NF-κB and HSF, and is more effective in these assays than the anti-psoriatic drugs, dimethylfumarate and methotrexate.

TABLE 3

| human keratinocytes | | | |
|---|---|---|---|
| Compounds | HSF | NF-κB | $LD_{50}$ |
| CTM-208 | 1.5 µM | 19 µM | 400 µM |
| Methotrexate | >400 µM | >400 µM | >400 µM |
| Dimethylfumarate | 50 µM | 20 µM | >400 µM |

TABLE 4

| human endothelial cells | | | |
|---|---|---|---|
| Compounds | HSF | NF-κB | $LD_{50}$ |
| CTM-208 | <1 µM | 5 µM | >400 µM |

GENERAL REMARKS

Figure 1:
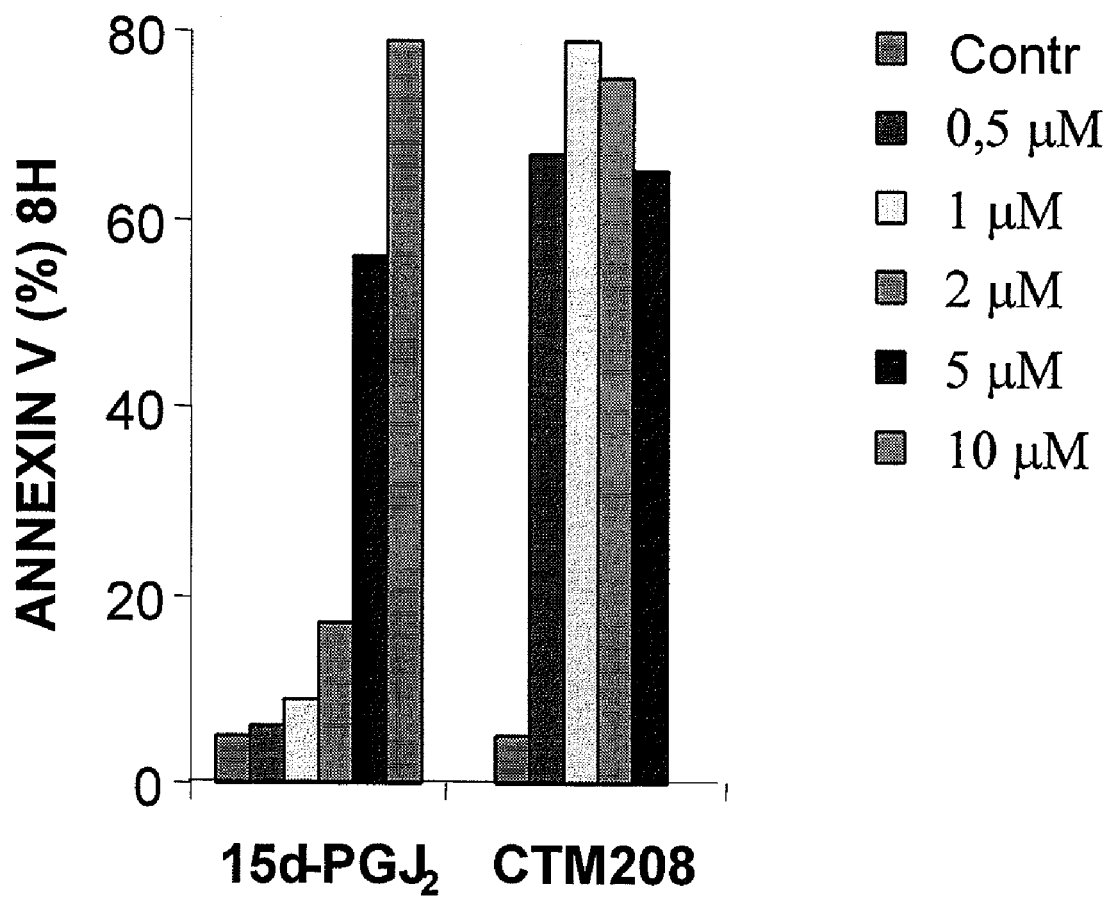
FIG. 1 shows the effect of a preferred compound of the invention, CTM-208, on induction of apoptosis in human Burkitt lymphoma HS-Sultan cells in comparison to the effect of the natural cyclopentenone prostanoid, 15-deoxy-$\Delta^{12,14}$-$PGJ_2$ (15d-$PGJ_2$). Apoptosis was measured by Annexin V staining, which detects the externalisation of phosphatidylserine, a characteristic feature of cells entering apoptosis.
Figure 2:
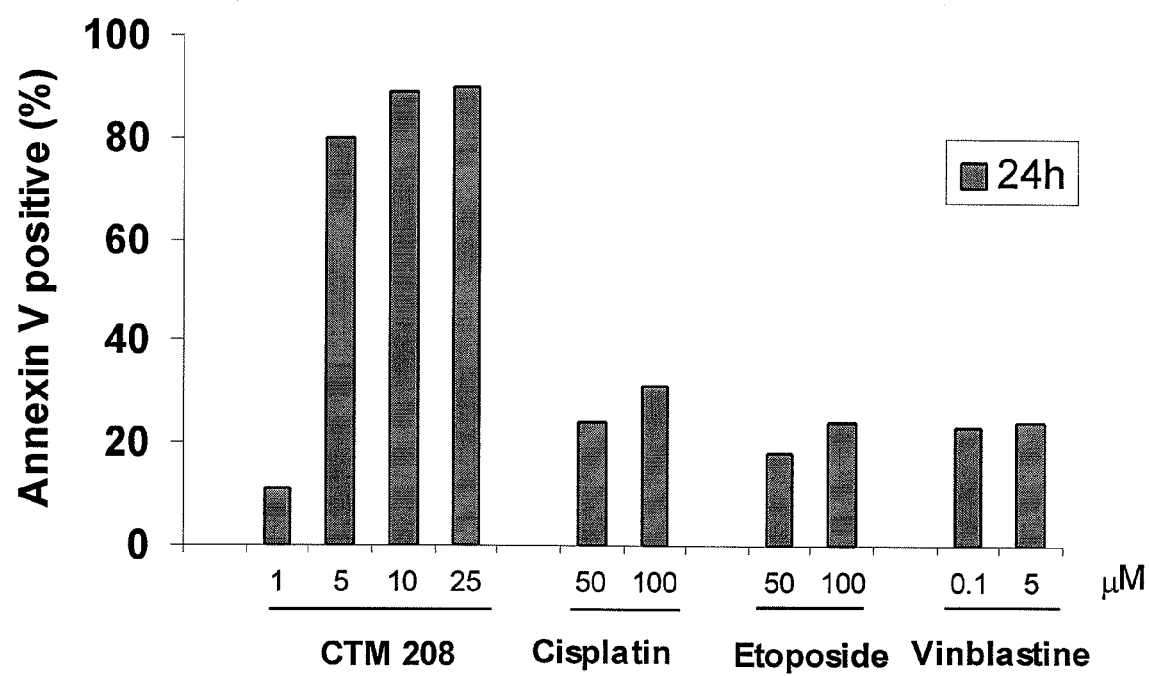
FIG. 2 shows the effect of CTM-208 on induction of apoptosis in human melanoma SK-MEL-28 cells in comparison to the effect of various chemotherapeutic agents, as measured by Annexin V staining.
Figure 3:
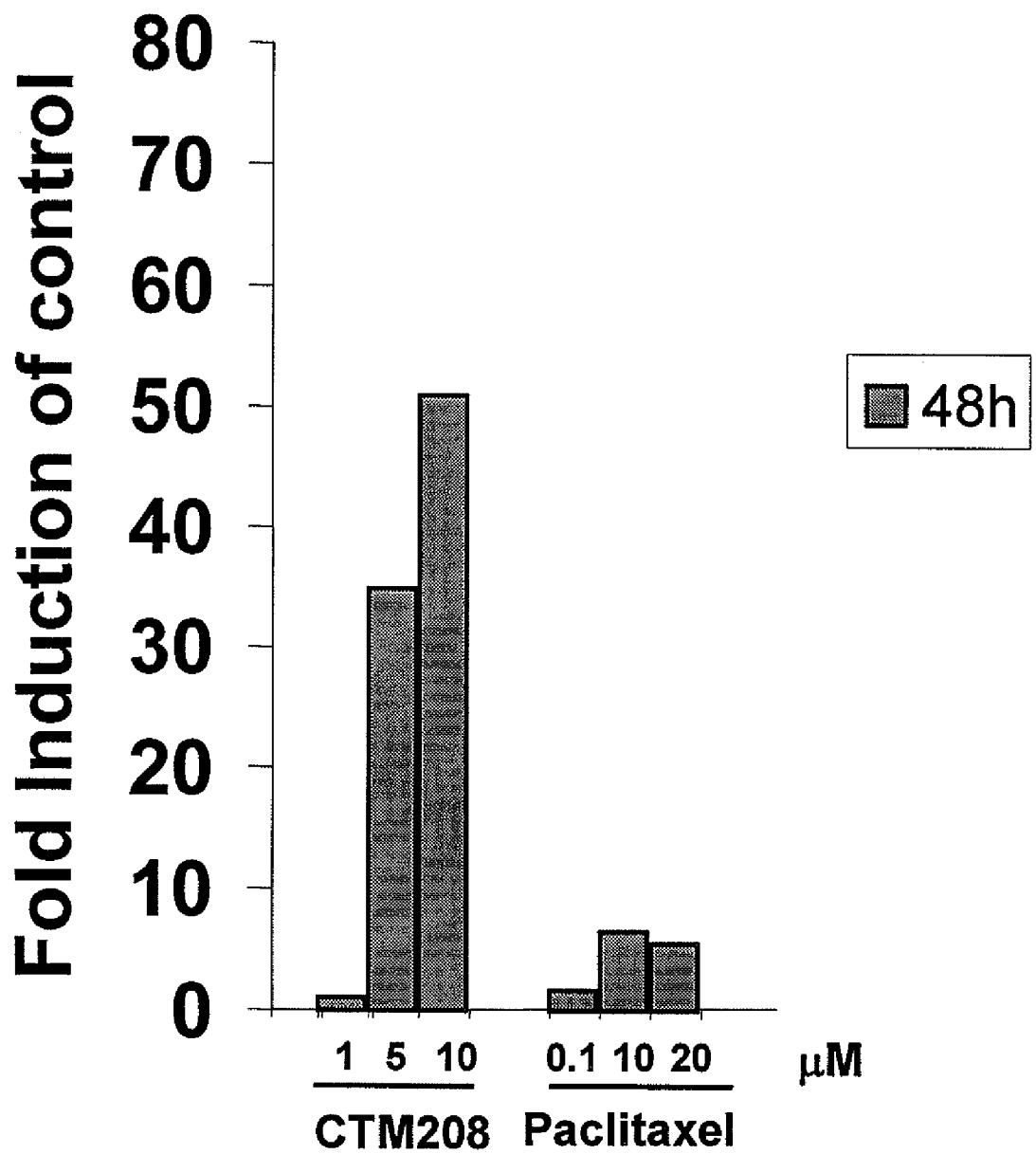
FIG. 3 shows the effect of CTM-208 on induction of DNA fragmentation in human breast cancer MDA-MB-231 cells in comparison to the effect of the chemotherapeutic agent, Paclitaxel.
Figure 4:
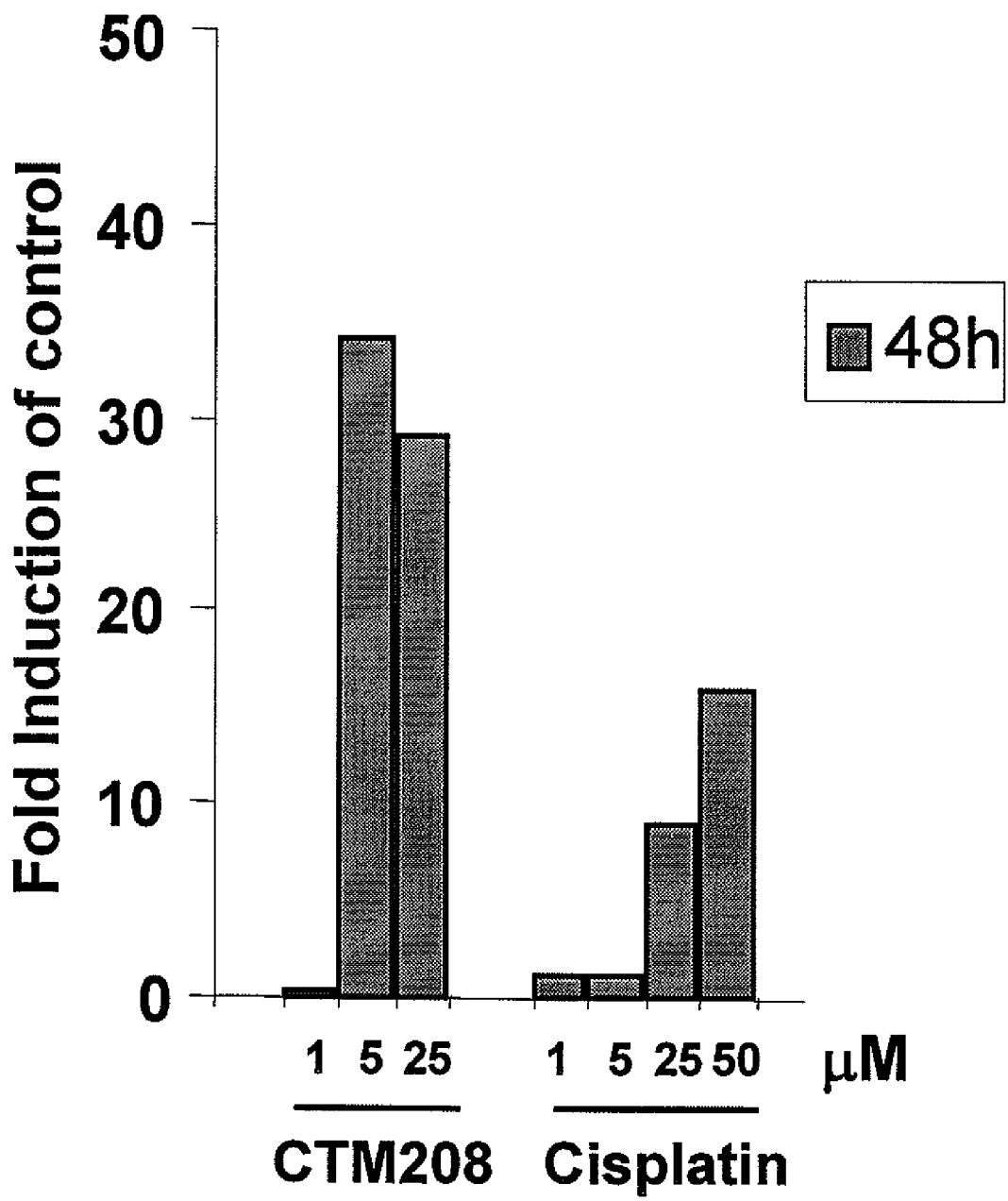
FIG. 4 shows the effect of CTM-208 on induction of DNA fragmentation in human melanoma SK-MEL-28 cells in comparison to the effect of the chemotherapeutic agent, Cisplatin.
Figure 5:
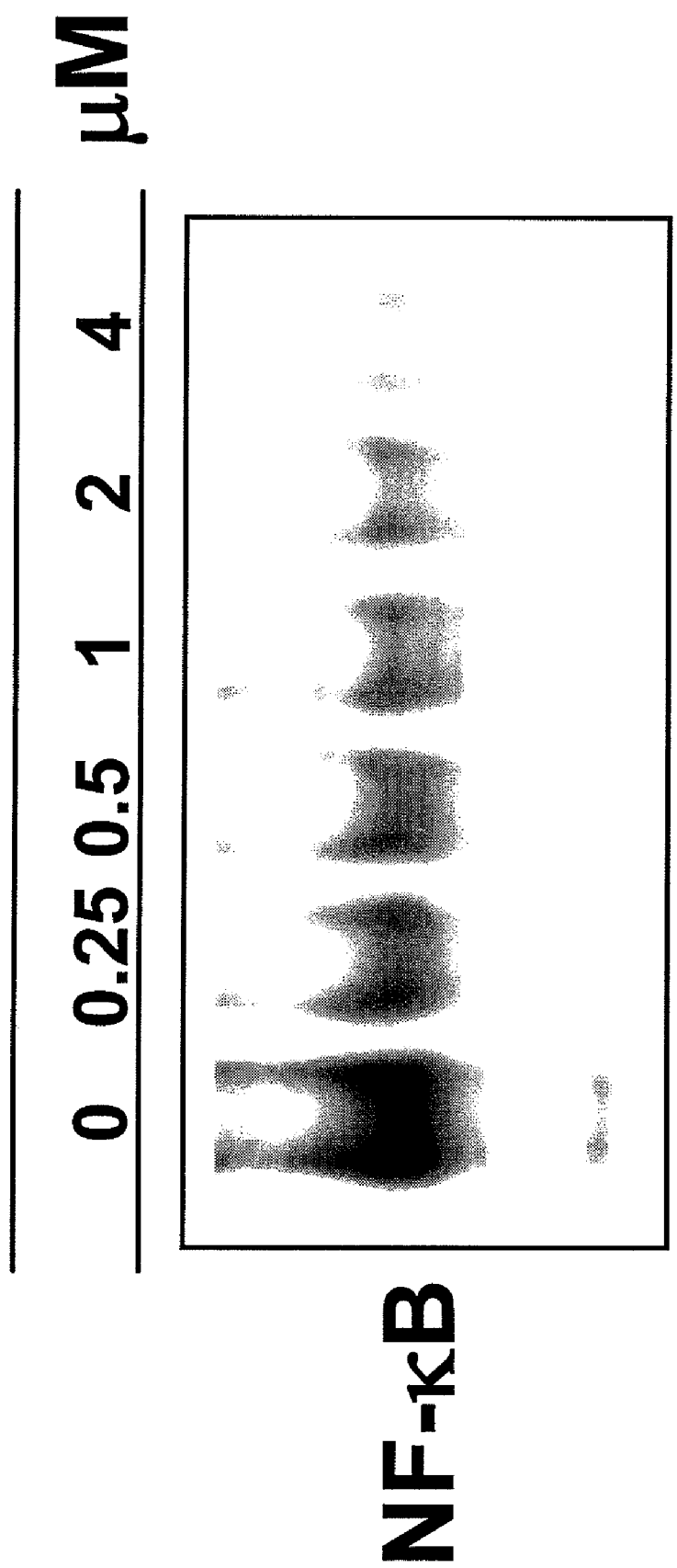
FIGS. 5 and 6 show the results of an EMSA (FIG. 5) and its quantitative determination (FIG. 6), in which whole-cell extracts from human Burkitt lymphoma HS-Sultan cells treated with CTM-208 were analysed for NF-κB DNA-binding activity.
Figure 6:
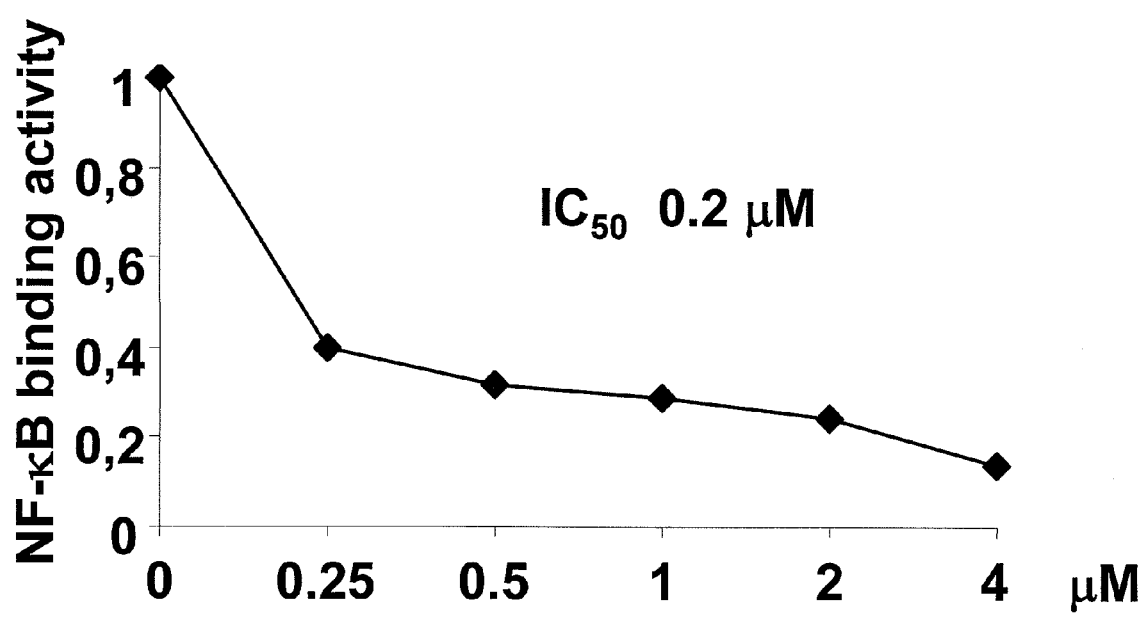
Figure 7:
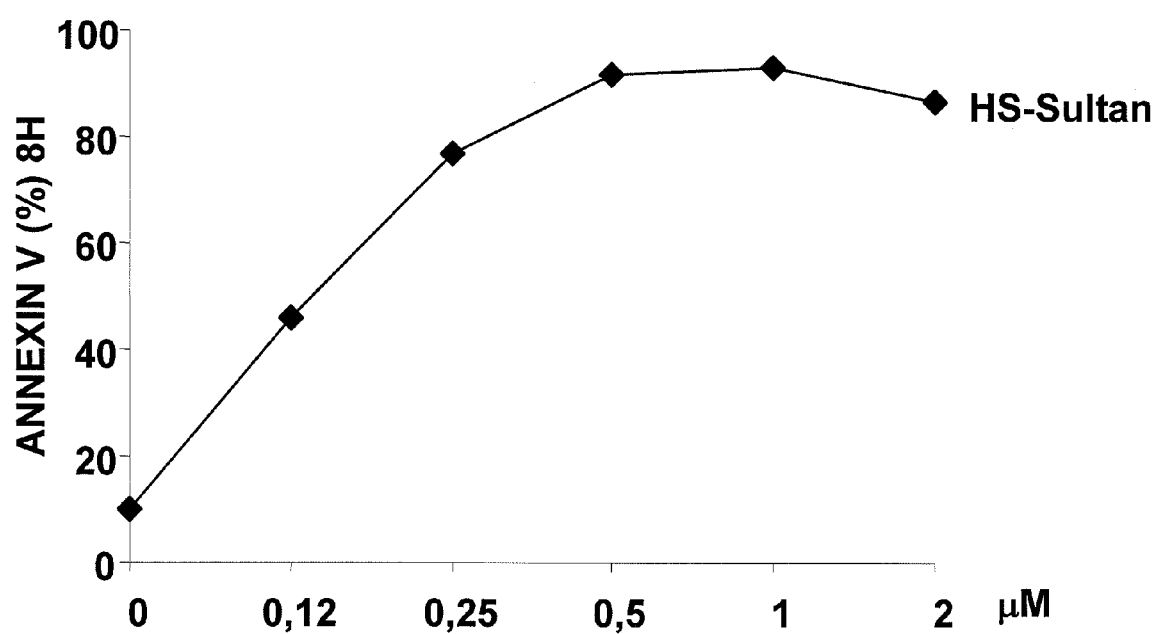
FIG. 7 shows the effect of CTM-208 on induction of apoptosis in the same cells.

The foregoing description of the invention is merely illustrative thereof and it should therefore be appreciated that various variations and modifications can be made without departing from the spirit or scope of the invention as set forth in the accompanying claims.

Where preferred or optional features are described in connection with particular aspects of the present invention, they shall be deemed to apply mutatis mutandis to other aspects of the invention unless the context indicates otherwise.

All documents cited herein are hereby incorporated by reference, as are any citations referred to in said documents.
References
1. Feige U, Morimoto R, Yahara I, Polia B S. *Stress-inducible Cellular Responses. Birkhaüser Verlag, Basel Boston Berlin,* 1996.
2. Marber M S, Walker J M, Latchman D S, 'Yellon D M. *J. Clin. Invest.* 93, 1087-1094, 1994.
3. Feinstein D L e al. *J. Biol. Chem.* 271, 17724-17732, 1996.
4. Amici C, Giorgi C, Rossi A, Santoro M G. *J. Virol* 68, 6890-6897, 1994.
5. Santoro M G, in *Stress-inducible Cellular Responses.* (Fiege U et al. eds, Birkhaüser Verlag, Basel Boston Berlin) pp. 337-357, 1996.
6. Santoro M G, Garaci 9, Amici C. *P.N.A.S. USA* 86, 8407-8411, 1989.
7. Amici C, Sistonen L, Santoro M G, Morimoto R I. *P.N.A.S. USA* 89, 6227-6231, 1992.
8. Santoro M G, Benedetto A. Carruba G, Garaci E, Jaffe B. *Science* 209, 1032-1034, 1980.
9. Santoro M G, *Trends Microbiol.* 5, 276-281, 1997.
10. Rozera C, Carattoli A, De Marco A, Amici C, Giorgi C, Santoro M G *J. Clin. Invest.* 97; 1795-1803, 1996.
11. Rossi A, Elia G, Santoro M G. *P.N.A.S. USA* 94, 746-750, 1997.
12. Thanos D, Maniatis T. *Cell* 80, 529-532, 1995.
13. Rossi A, Elia G, Santoro M G. *J. Biol. Chem.* 271, 32192-32196, 1996.
14. Shield M J. *Pharmacol. Ther.* 65, 125-137, 1995.
15. Sinclair S B et al. *J. Clin. Invest.* 84, 1063-1067, 1989.
16. Baeuerle P A and Henkel T (1994). Function and Activation of NF-Kappa B in the Immune System. Annual Reviews of Immunology 12: 141-179.
17. Colville-Nash P R et al. (1998). Inhibition of Inducible Nitric Oxide Synthase by Peroxisome Proliferator-Activated Receptor Agonists: Correlation with Induction of Heme Oxygenase 1. Journal of Immunology 161, 978-984.
18. K. J. Stone, R. D. Little, JOC, 1984, 49, 1849-1853.
19. A. Kawamoto, H. Kosugi, H. Uda, Chem. Lett., 1972, 807-810.
20. Moriguchi I, Hirono S, Liu Q, Nakagome Y, and Matsushita Y, (1992) Simple method of calculating octanol/water partition coefficient. Chem. Pharm. Bull. 40, 127-130.
21. Lipinski C, Lombardo F, Dominy B, Feeney P, (1997) Experimental and computational approaches to estimate solubility and permeability in drug discovery and development settings. Advanced Drug Delivery Reviews 23 (1997) 3-25.
22. Kondo, M.; Oya-Ito, T.; Kumagai, T.; Osawa, T.; Uchida, K. *J. Biolog. Chem.* 2001, 296, 12076-12083.
23. Silverman, R. B., In *The Organic Chemistry of Drug Design and Drug Action*; Academic Press; A Harcourt Science and Technology Company: San Diego, 1992, 336-338.
24. R. J. Flanagan, *Chemistry in Britain,* 2002, 28.
25. Meister, A., Anderson, M., E., *Ann. Rev. Biochem.* 1983, 52, 711-760.

The invention claimed is:
1. A compound of II:

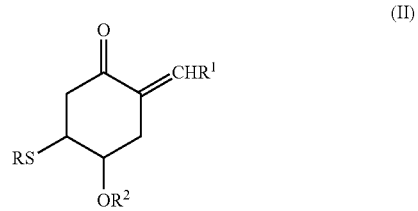

wherein:
R is an alkyl, alkenyl, alkynyl, aryl, aralkyl, aralkenyl, or aralkynyl group, that may be substituted or unsubstituted, and that optionally includes at least one heteroatom in its carbon skeleton;
$R^1$ is hydrogen, or an alkyl, substituted alkyl, alkenyl, alkynyl, aryl, substituted aryl, or aralkyl group; and
$R^2$ is an alkyl, alkenyl, alkynyl, aryl, aralkyl, aralkenyl, or aralkynyl group containing 4-12 carbon atoms, that may be substituted or unsubstituted, and that optionally includes at least one heteroatom in its carbon skeleton; not an acetyl or tert-butyldimethylsilyl group.
2. A compound of formula II as claimed in claim 1, wherein:
(a) R is an $R^3CH_2$— group, wherein $R^3$ is an alkyl, alkenyl, alkynyl, aryl, aralkyl, aralkenyl, or aralkynyl group, that may be substituted or unsubstituted, and that optionally includes at least one heteroatom in its carbon skeleton;
(b) R contains 1-12 carbon atoms;
(c) R includes at least one hydrophilic group;
(d) R includes at least one hydrophilic group which is or includes a hydroxyl, carbonyl, carboxyl, amino, amido, quaternary ammonium or thiolyl group;
(e) R includes at least one hydrophilic group and provides the functionality of an amine, amide, peptide, ester, carboxylic acid, carboxylic acid salt, alcohol, aldehyde, ketone or thiol;
(f) the group —SR is an S-cysteinyl or a substituted S-cysteinyl group;
(g) the group —SR is a substituted S-cysteinyl group which is a di- or tri-peptide group that includes an S-cysteinyl moiety; or
(h) the group —SR is a substituted S-cysteinyl group which is an S-glutathionyl, N-tert-butoxycarbonyl S-cysteinyl or N-tert-butoxycarbonyl S-cysteinyl ester group.
3. A compound as claimed in claim 1, wherein:
(a) $R^1$ is an aryl group; or
(b) $R^1$ is a phenyl group or a substituted phenyl group.
4. A compound as claimed in claim 1, wherein:
(a) $R^2$ is an alkyl group that includes a heteroatom in its carbon skeleton;
(b) $R^2$ is an alkyl group that includes a silicon atom in its carbon skeleton;
(c) $R^2$ is a trialkylsilyl group;
(d) $R^2$ is a tert-butyldimethylsilyl group;

(e) $R^2$ is —$COR^5$, wherein $R^5$ is an alkyl, alkenyl, alkynyl, aryl, aralkyl, aralkenyl, or aralkynyl group containing 3-11 carbon atoms, that may be substituted or unsubstituted, and that optionally includes at least one heteroatom in its carbon skeleton;
(f) $R^2$ is —$COR^5$, wherein $R^5$ is an alkyl group containing 3-6 carbon atoms; or
(g) $R^2$ is —$COR^5$, wherein $R^5$ is a tert-butyl group.

5. A compound of formula II as claimed in claim 1, having a calculated or measured Log P value that is at least 0.25, 0.5, 0.75, 1 or 1.25 higher or lower than the log P value for the equivalent compound of formula I, wherein the log P values for said compounds are calculated or measured using the same technique.

6. A compound as claimed in claim 1:
(a) that is pharmaceutically or therapeutically active; or
(b) having activity in respect of one or more of the following: (i) activating HSF; (ii) inhibiting NF-κB; (iii) inhibiting the replication of HSV-1; (iv) inhibiting the replication of Sendai virus; (v) inducing apoptosis in cancer cell lines; and (vi) anti-angiogenic activity.

7. A pharmaceutical composition comprising a compound as claimed in claim 1 and optionally including a pharmaceutically acceptable carrier.

8. A food for an aquatic organism comprising a compound as claimed in claim 1.

9. An aquatic environment comprising a compound as claimed in claim 1.

10. The compound of claim 1, wherein the compound is CTM-208 represented by the formula:

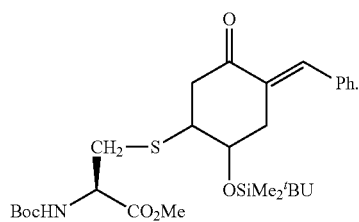

* * * * *